(12) United States Patent
Toshimori et al.

(10) Patent No.: US 8,741,583 B2
(45) Date of Patent: Jun. 3, 2014

(54) METHOD OF IDENTIFYING COMPOUNDS THAT INHIBIT FERTILIZATION

(75) Inventors: Kiyotaka Toshimori, Chiba (JP); Chizuru Ito, Chiba (JP); Kenji Yamatoya, Chiba (JP); Keiichi Yoshida, Chiba (JP)

(73) Assignee: National University Corporation Chiba University, Chiba (JP)

( * ) Notice: Subject to any disclaimer, the term of this patent is extended or adjusted under 35 U.S.C. 154(b) by 0 days.

(21) Appl. No.: 13/379,459

(22) PCT Filed: Mar. 31, 2010

(86) PCT No.: PCT/IB2010/051391
§ 371 (c)(1),
(2), (4) Date: Jan. 30, 2012

(87) PCT Pub. No.: WO2010/150110
PCT Pub. Date: Dec. 29, 2010

(65) Prior Publication Data
US 2012/0122244 A1    May 17, 2012

Related U.S. Application Data

(60) Provisional application No. 61/220,367, filed on Jun. 25, 2009.

(51) Int. Cl.
*G01N 33/53* (2006.01)
(52) U.S. Cl.
USPC .......................................... 435/7.1; 436/518
(58) Field of Classification Search
None
See application file for complete search history.

(56) References Cited

U.S. PATENT DOCUMENTS 7,682,800 B2 * 3/2010 Gelboin et al. ................ 435/7.1

OTHER PUBLICATIONS

Li et al. FEBS Letters 2006 vol. 580, p. 466-472.*
International Search Report issued in corresponding International Patent Application No. PCT/IB2010/051391 dated Jun. 18, 2010 (2 pages).
Toshimori et al., "An MN9 Antigenic Molecule, Equatorin, Is Required for Successful Sperm-Oocyte Fusion in Mice," Biology of Reproduction, vol. 59, 1998, pp. 22-29.
Yoshinaga et al., "Inhibition of mouse fertilization in vivo by intra-oviductal injection of an anti-equatorin monoclonal antibody," Reproduction, vol. 122, 2001, pp. 649-655.
Yoshida et al., "Mouse Sperm Equatorin Analyzed by Anti-Equatorin Antibodies, MN9 and EQ70-83," Biology of Reproduction, vol. 78, Jan. 1, 2008, Abstract only (2 pages).
Yamatoya et al., "Mammalian Sperm MN9 Antigen N-,O-sialoglycoprotein Equatorin: Biochemical Characterization and Identification of the Gene," Biology of Reproduction, vol. 78, Jan. 1, 2008, Abstract only (2 pages).
Yamatoya et al., "Equatorin: Identification and Characterization of the Epitope of the MN9 Antibody in the Mouse," Biology of Reproduction, vol. 81, 2009, pp. 889-897.

* cited by examiner

*Primary Examiner* — Jacob Cheu
(74) *Attorney, Agent, or Firm* — Kilyk & Bowersox, P.L.L.C.

(57) ABSTRACT

A method of identifying compounds that inhibit fertilization is provided. The method can include selecting compounds that bind to equatorin protein. Two types of equatorin protein, a long form and a short form, can be present in the testis. The amino acid sequence of mouse equatorin from positions 101 to 146 including the 138th O-glycosylated threonine residue contains an epitope recognized by anti-equatorin antibody MN9 that has an effect of inhibiting fertilization. In addition, the MN9 antibody also binds to human sperm. Compounds that bind to the epitope can inhibit fertilization. Both forms of mouse equatorin can be used as well as human equatorin to identify compounds that inhibit fertilization.

9 Claims, 10 Drawing Sheets

Figure 2

METHOD OF IDENTIFYING COMPOUNDS THAT INHIBIT FERTILIZATION

This application is a National Phase Entry of International Application No. PCT/IB2010/051391 filed Mar. 31, 2010, which claims the benefit of prior U.S. Provisional Patent Application No. 61/220,367, filed Jun. 25, 2009, which is incorporated in its entirety by reference herein.

BACKGROUND OF THE INVENTION

It is to be understood that the numbers appearing in brackets ([ ]) throughout this application refer to the numbers that correspond to the References appearing at the end of this section.

Among the few molecules known to be vital for sperm-egg fusion are sperm Izumo1 [1] and egg CD9 [2-4]. Izumo1 is a type 1 transmembrane protein localized to the acrosome before the acrosome reaction, and it relocates onto the sperm surface after the acrosome reaction [1]. The details of the molecular mechanisms involved in this process remain unclear. A tetraspanin molecule, CD9 is expressed on the oolemma, but the nature of the CD9-sperm ligand interaction remains unclear. Several other gamete fusion candidate molecules have been identified; however, gene deletion studies have shown that they are not essential in sperm-egg fusion, although their roles may be substituted or bypassed by other proteins. These molecules include ADAM1, 2, and 3—also known as fertilin-α, fertilin-β, and cyritestin, respectively [5-8]—in addition to CRISP1 (DE) [9] and CD46 [10]. Other candidate molecules required for sperm-egg fusion have been reported, and their functions have been studied by specific antibody inhibition assays. These include equatorin (EQT)—also known as MN9 antigen [11, 12]—SPESP1 (ESP) [13, 14], SPACA4 (SAMP14) [15], SPACA1 (SAMP32) [16], and SPACA3 (SLLP1) [17]. Thus, the molecular mechanisms underlying sperm-egg fusion remain an open question.

Some of the major difficulties in analyzing the molecular mechanisms underlying sperm-egg fusion include the biochemical nature and localization of the sperm proteins. In fact, it has been shown that sperm glycoproteins have unique carbohydrate chains and show continuous modifications after spermiation until the sperm-egg interaction [18-22]. In addition, the localization of some sperm proteins changes during the acrosome reaction, as seen with equatorin [23], Izumo1 [1] and SPACA4 [15]; these molecules are translocated from the acrosomal matrix to the cell surface. These modifications are thought to be important steps, priming sperm molecules for the sperm-egg interaction.

Equatorin is a widely distributed acrosomal protein in mammalian sperm. The present inventors previously reported that the MN9 antigen equatorin was widely distributed in mammals, including humans, and showed a strong affinity for the equatorial region of the acrosome [24]; thus, the MN9 antigen was renamed equatorin. Functionally, the anti-equatorin antibody MN9 inhibits the release of cortical granules without inhibiting zona penetration and sperm-egg binding, suggesting that it inhibits sperm-egg fusion or an early stage of egg activation [11]. The MN9 antibody inhibits sperm-egg interaction not only in vitro but also in vivo [12]. During the acrosome reaction, equatorin translocates to the plasma membrane, covering the equatorial segment as seen with immunogold staining [23]. The plasma membrane over the equatorial segment is known to fuse with the plasma membrane of egg microvilli [25-28].

Based on these finding, the present inventors determined that the equatorin gene needed to be identified and the biochemical nature and localization of the equatorin protein needed to be clarified. In particular, the nature of the epitope region of the MN9 antibody (MN9 epitope) needed to be understood, to determine whether this region is involved in the sperm-egg interaction.

REFERENCES

1. Inoue N, Ikawa M, Isotani A, Okabe M. The immunoglobulin superfamily protein Izumo is required for sperm to fuse with eggs. Nature 2005; 434: 234-238.
2. Kaji K, Oda S, Shikano T, Ohnuki T, Uematsu Y, Sakagami J, Tada N, Miyazaki S, Kudo A. The gamete fusion process is defective in eggs of Cd9-deficient mice. Nat Genet 2000; 24: 279-282.
3. Le Naour F, Rubinstein E, Jasmin C, Prenant M, Boucheix C. Severely reduced female fertility in CD9-deficient mice. Science 2000; 287: 319-321.
4. Miyado K, Yamada G, Yamada S, Hasuwa H, Nakamura Y, Ryu F, Suzuki K, Kosai K, Inoue K, Ogura A, Okabe M, Mekada E. Requirement of CD9 on the egg plasma membrane for fertilization. Science 2000; 287: 321-324.
5. Nishimura H, Kim E, Nakanishi T, Baba T. Possible function of the ADAM1a/ADAM2 Fertilin complex in the appearance of ADAM3 on the sperm surface. J Biol Chem 2004; 279: 34957-34962.
6. Cho C, Bunch D O, Faure J E, Goulding E H, Eddy E M, Primakoff P, Myles D G. Fertilization defects in sperm from mice lacking fertilin beta. Science 1998; 281: 1857-1859.
7. Nishimura H, Cho C, Branciforte D R, Myles D G, Primakoff P. Analysis of loss of adhesive function in sperm lacking cyritestin or fertilin beta. Dev Biol 2001; 233: 204-213.
8. Shamsadin R, Adham I M, Nayernia K, Heinlein U A, Oberwinkler H, Engel W. Male mice deficient for germ-cell cyritestin are infertile. Biol Reprod 1999; 61: 1445-1451.
9. Da Ros V G, Maldera J A, Willis W D, Cohen D J, Goulding E H, Gelman D M, Rubinstein M, Eddy E M, Cuasnicu P S. Impaired sperm fertilizing ability in mice lacking Cysteine-RIch Secretory Protein 1 (CRISP1). Dev Biol 2008; 320: 12-18.
10. Inoue N, Ikawa M, Nakanishi T, Matsumoto M, Nomura M, Seya T, Okabe M. Disruption of mouse CD46 causes an accelerated spontaneous acrosome reaction in sperm. Mol Cell Biol 2003; 23: 2614-2622.
11. Toshimori K, Saxena D K, Tanii I, Yoshinaga K. An MN9 antigenic molecule, equatorin, is required for successful sperm-oocyte fusion in mice. Biol Reprod 1998; 59: 22-29.
12. Yoshinaga K, Saxena D K, Oh-oka T, Tanii I, Toshimori K. Inhibition of mouse fertilization in vivo by intra-oviductal injection of an anti-equatorin monoclonal antibody. Reproduction 2001; 122: 649-655.
13. Wolkowicz M J, Shetty J, Westbrook A, Klotz K, Jayes F, Mandal A, Flickinger C J, Herr J C. Equatorial segment protein defines a discrete acrosomal subcompartment persisting throughout acrosomal biogenesis. Biol Reprod 2003; 69: 735-745.
14. Wolkowicz M J, Digilio L, Klotz K, Shetty J, Flickinger C J, Herr J C. Equatorial segment protein (ESP) is a human alloantigen involved in sperm-egg binding and fusion. J Androl 2008; 29: 272-282.
15. Shetty J, Wolkowicz M J, Digilio L C, Klotz K L, Jayes F L, Diekman A B, Westbrook V A, Farris E M, Hao Z, Coonrod S A, Flickinger C J, Herr J C. SAMP14, a novel, acrosomal membrane-associated, glycosylphosphatidylinositol-anchored member of the Ly-6/Urokinase-type plasminogen activator receptor superfamily with a role in sperm-egg interaction. J Biol Chem 2003; 278: 30506-30515.

16. Hao Z, Wolkowicz M J, Shetty J, Klotz K, Bolling L, Sen B, Westbrook V A, Coonrod S, Flickinger C J, Herr J C. SAMP32, a testis-specific, isoantigenic sperm acrosomal membrane-associated protein. Biol Reprod 2002; 66: 735-744.

17. Herrero M B, Mandal A, Digilio L C, Coonrod S A, Maier B, Herr J C. Mouse SLLP1, a sperm lysozyme-like protein involved in sperm-egg binding and fertilization. Dev Biol 2005; 284: 126-142.

18. Aitken R J, Baker M A. The role of proteomics in understanding sperm cell biology. Int J Androl 2008; 31: 295-302.

19. Diekman A B, Norton E J, Klotz K L, Westbrook V A, Shibahara H, Naaby-Hansen S, Flickinger C J, Herr J C. N-linked glycan of a sperm CD52 glycoform associated with human infertility. FASEB J 1999; 13: 1303-1313.

20. Toshimori K. Maturation of mammalian spermatozoa: modifications of the acrosome and plasma membrane leading to fertilization. Cell Tissue Res 1998; 293: 177-187.

21. Toshimori K. Dynamics of the Mammalian Sperm Head: Modifications and Maturation Events From Spermatogenesis to Egg Activation. Berlin Heidelberg: Springer-Verlag; 2009.

22. Toshimori K, Maekawa M, Ito C, Toyama Y, Suzuki-Toyota F, Saxena D K. The involvement of immunoglobulin superfamily proteins in spermatogenesis and sperm-egg interaction. Reproductive Medicine and Biology 2006; 5: 87-93.

23. Manandhar G, Toshimori K. Exposure of sperm head equatorin after acrosome reaction and its fate after fertilization in mice. Biol Reprod 2001; 65: 1425-1436.

24. Toshimori K, Tanii I, Araki S, Oura C. Characterization of the antigen recognized by a monoclonal antibody MN9: unique transport pathway to the equatorial segment of sperm head during spermiogenesis. Cell Tissue Res 1992; 270: 459-468.

25. Bedford J M, Moore H D, Franklin L E. Significance of the equatorial segment of the acrosome of the spermatozoon in eutherian mammals. Exp Cell Res 1979; 119: 119-126.

26. Oura C, Toshimori K. Ultrastructural studies on the fertilization of mammalian gametes. Int Rev Cytol 1990; 122: 105-151.

27. Toshimori K. Penetration of the mouse sperm head through the zona pellucida in vivo: an electronmicroscope study at 200 KV. Biol Reprod 1982; 26: 475-481.

28. Yanagimachi R, Noda Y D. Physiological changes in the postnuclear cap region of mammalian spermatozoa: a necessary preliminary to the membrane fusion between sperm and egg cells. J Ultrastruct Res 1970; 31: 486-493.

29. Kuan S F, Byrd J C, Basbaum C, Kim Y S. Inhibition of mucin glycosylation by aryl-N-acetyl-alpha-galactosaminides in human colon cancer cells. J. Biol. Chem. 1989; 264: 19271-19277.

30. Tsukamoto H, Yoshitake H, Mori M, Yanagida M, Takamori K, Ogawa H, Takizawa T, Araki Y. Testicular proteins associated with the germ cell-marker, TEX101: involvement of cellubrevin in TEX101-trafficking to the cell surface during spermatogenesis. Biochem Biophys Res Commun 2006; 345: 229-238.

31. Altschul S F, Madden T L, Schaffer A A, Zhang J, Zhang Z, Miller W, Lipman D J. Gapped BLAST and PSI-BLAST: a new generation of protein database search programs. Nucleic Acids Res 1997; 25: 3389-3402.

32. Notredame C, Higgins D G, Hering a J. T-Coffee: A novel method for fast and accurate multiple sequence alignment. J Mol Biol 2000; 302: 205-217.

33. Poirot O, O'Toole E, Notredame C. Tcoffee@igs: A web server for computing, evaluating and combining multiple sequence alignments. Nucleic Acids Res 2003; 31: 3503-3506.

34. Bendtsen J D, Nielsen H, von Heijne G, Brunak S. Improved prediction of signal peptides: SignalP 3.0. J Mol Biol 2004; 340: 783-795.

35. Nielsen H, Engelbrecht J, Brunak S, von Heijne G Identification of prokaryotic and eukaryotic signal peptides and prediction of their cleavage sites. Protein Eng 1997; 10: 1-6.

36. Krogh A, Larsson B, von Heijne G, Sonnhammer E L. Predicting transmembrane protein topology with a hidden Markov model: application to complete genomes. J Mol Biol 2001; 305: 567-580.

37. Sonnhammer E L, von Heijne G Krogh A. A hidden Markov model for predicting transmembrane helices in protein sequences. Proc Int Conf Intell Syst Mol Biol 1998; 6: 175-182.

38. Toyoda Y, Yokoyama M, Hoshi T. Studies on the fertilization of mouse eggs in vitro. I. In vitro fertilization of eggs by fresh epididymal sperm. Jpn J Anim Reprod 1971; 16: 147-151.

39. Chiang C F, Okou D T, Griffin T B, Verret C R, Williams M N. Green fluorescent protein rendered susceptible to proteolysis: positions for protease-sensitive insertions. Arch Biochem Biophys 2001; 394: 229-235.

40. Miyata S, Sato C, Kumita H, Toriyama M, Vacquier V D, Kitajima K. Flagellasialin: a novel sulfated alpha2,9-linked polysialic acid glycoprotein of sea urchin sperm flagella. Glycobiology 2006; 16: 1229-1241.

41. Kingsley D M, Kozarsky K F, Hobbie L, Krieger M. Reversible defects in O-linked glycosylation and LDL receptor expression in a UDP-Gal/UDP-GalNAc 4-epimerase deficient mutant. Cell 1986; 44: 749-759.

42. Reddy P, Caras I, Krieger M. Effects of O-linked glycosylation on the cell surface expression and stability of decay-accelerating factor, a glycophospholipid-anchored membrane protein. J Biol Chem 1989; 264: 17329-17336.

43. Tarentino A L, Gomez C M, Plummer T H, Jr. Deglycosylation of asparagine-linked glycans by peptide:N-glycosidase F. Biochemistry 1985; 24: 4665-4671.

44. Uchida Y, Tsukada Y, Sugimori T. Enzymatic properties of neuraminidases from *Arthrobacter ureafaciens*. J Biochem 1979; 86: 1573-1585.

SUMMARY OF THE PRESENT INVENTION

The present invention relates to a method of identifying compounds that inhibit fertilization. The method can comprise selecting compounds that bind to equatorin protein. Two types of equatorin protein, a long form and a short form, can be present in the testis. The amino acid sequence of mouse equatorin from positions 101 to 146 including the $138^{th}$ O-glycosylated threonine residue contains an epitope recognized by anti-equatorin antibody MN9 that has an effect of inhibiting fertilization. In addition, the MN9 antibody also binds to human sperm. Compounds that bind to the epitope can inhibit fertilization. In the identification method of the present invention, both forms of mouse equatorin can be used as well as human equatorin to identify compounds that inhibit fertilization.

A feature of the present invention is to provide a method of identifying a compound that can inhibit fertilization. The method can comprise selecting a compound that binds to a region of mouse equatorin that contains an O-glycosylated threonine residue located at position 138 of the amino acid sequence of SEQ ID NO: 2 or SEQ ID NO: 3, or a region of human equatorin that contains an O-glycosylated threonine residue located at position 136 of the amino acid sequence of SEQ ID NO: 5. The region of mouse equatorin can be a region comprising the amino acid sequence from position 101 to position 146 in the amino acid sequence of SEQ ID NO: 3 or SEQ ID NO:4 of mouse equatorin, and the region of human equatorin can be a region comprising the amino acid sequence from position 92 to position 144 in the amino acid sequence of SEQ ID NO: 5 of human equatorin.

It is to be understood that both the foregoing general description and the following detailed description are exemplary and explanatory only and are intended to provide a further explanation of the present invention, as claimed.

The accompanying drawings, which are incorporated in and constitute a part of this application, illustrate some of the embodiments of the present invention and together with the description, serve to explain the principles of the present invention.

BRIEF DESCRIPTION OF THE DRAWINGS

FIG. 2. Amino acid sequence of equatorin identified by LC-MS/MS and alignment of human and mouse equatorin.

DETAILED DESCRIPTION OF THE PRESENT INVENTION

Figure 1:
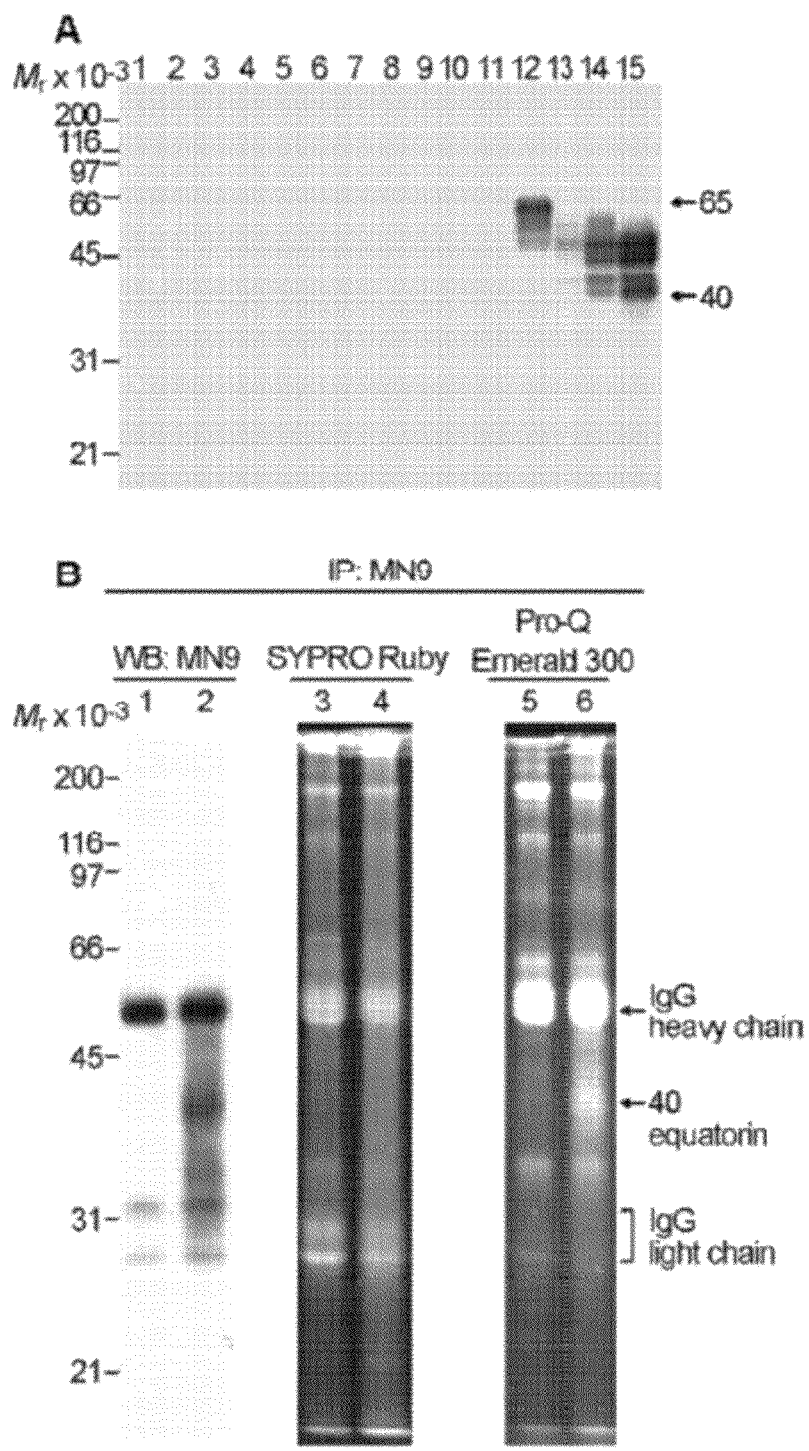
FIG. 1A. Distribution of equatorin in various tissues. Western blot (12.5% gel) with MN9 antibody.
FIG. 1B. Purification for LC-MS/MS analysis and in-gel detection of equatorin. Immunoprecipitation (IP) with MN9 antibody. Separation by 10% gel SDS-PAGE.
Figure 3:
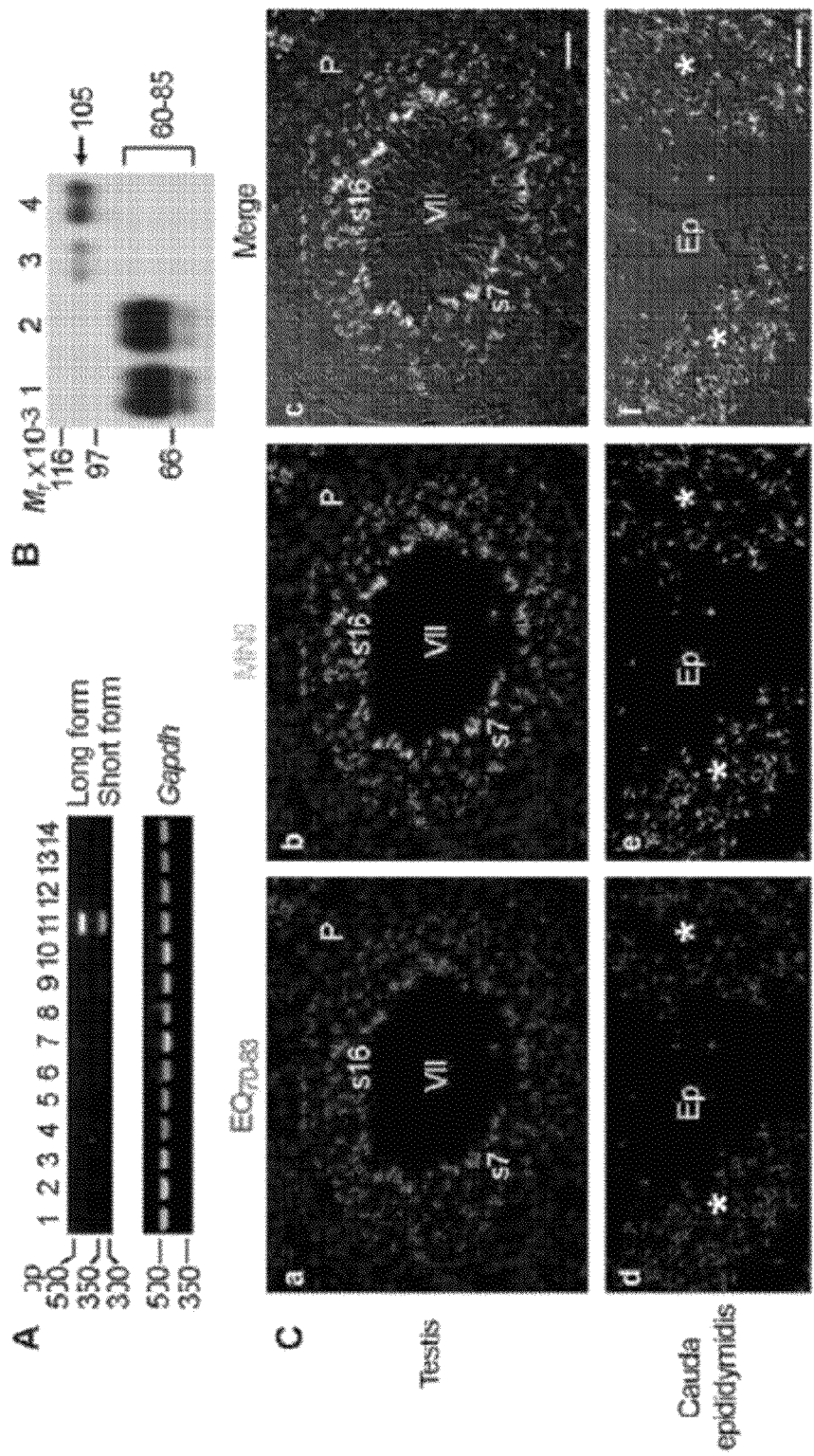
FIG. 3A. Expression of equatorin and verification study using recombinant protein in HEK293T cells. Expression of mRNA in various tissues by RT-PCR.
FIG. 3B. Western blot analysis with the MN9 antibody indicating detection of recombinant equatorin.
FIG. 3C. Images showing distribution of equatorin in the testis and cauda epididymidis, obtained using IIF microscopy with $EQ_{70-83}$ antibody and MN9 antibody.

Abbreviations used: aa, amino acid(s); Benzyl-α-GalNAc, benzyl-2-acetamido-2-deoxy-α-D-galactopyranoside; CIAP, calf intestinal alkaline phosphatase; EQT, equatorin; Gapdh, glyceraldehyde-3-phosphate dehydrogenase; IIF, indirect immunofluorescence; IRES, internal ribosome entry site; LC-MS/MS, liquid chromatography tandem mass spectrometry.

The present invention relates to a method of identifying compounds that inhibit fertilization. The method can comprise selecting compounds that bind to equatorin protein. Equatorin is a widely distributed acrosomal protein in mammalian sperm. The present inventors have cloned mouse equatorin gene and found that two types of equatorin protein, a long form (SEQ ID NO: 3) and a short form (SEQ ID: 2), are present in the testis. The amino acid sequence of mouse equatorin (SEQ ID NO: 2 or SEQ ID NO: 3) from positions 101 to 146 including the 138$^{th}$ O-glycosylated threonine residue contains an epitope recognized by anti-equatorin antibody MN9 that has an effect of inhibiting fertilization. In addition, the present inventors found that MN9 antibody also binds to human sperm by using Western blot and Indirect immunofluorescence analysis, which indicates that MN9 antibody binds to human equatorin (SEQ ID NO:5). As such, compounds that bind to the epitope can inhibit fertilization. In the identification method of the present invention, both forms of mouse equatorin can be used as well as human equatorin.

Equatorin (MN9 antigenic molecule) is a widely distributed acrosomal protein in mammalian sperm. Some amount of equatorin translocates to the plasma membrane covering the equatorial region during the acrosome reaction. From studies of both in vitro and in vivo fertilization inhibition using the MN9 antibody, equatorin has been suggested to be involved in fusion with the oolemma. In this study we cloned equatorin and found it to be a highly glycosylated protein using mass spectrometry and carbohydrate staining. Equatorin is a sperm-specific type 1 transmembrane protein, and glycosidase treatment and recombinant protein assays verified that it is an N,O-sialoglycoprotein. In addition, the gamete interaction-related domain recognized by the MN9 antibody is post-translationally modified. The modified domain was identified near threonine 138, which was most likely to be O-glycosylated when analyzed by amino acid substitution, dephosphorylation and O-glycosylation inhibitor assays. Immunogold electron microscopy localized the equatorin N-terminus, where the MN9 epitope is present, on the acrosomal membrane facing the acrosomal lumen. These biochemical properties and the localization of equatorin are important for further analysis of the translocation mechanism leading to gamete interaction.

The method of identifying a compound that inhibits fertilization can comprise selecting a compound that binds to a region of mouse equatorin that contains an O-glycosylated threonine residue located at position 138 of the amino acid sequence of SEQ ID NO: 2 or SEQ ID NO: 3, or a region of human equatorin that contains an O-glycosylated threonine residue located at position 136 of the amino acid sequence of SEQ ID NO: 5. The region of mouse equatorin can be a region comprising the amino acid sequence from position 101 to position 146 in the amino acid sequence of SEQ ID NO: 3 or SEQ ID NO: 4 of mouse equatorin. The region of human equatorin can be a region comprising the amino acid sequence from position 92 to position 144 in the amino acid sequence of SEQ ID NO: 5 of human equatorin. The method of identifying a compound that inhibits fertilization can comprise: (1) contacting mouse equatorin or human equatorin with a test compound; (2) detecting binding of an antibody that recognizes said region to the mouse equatorin or the human equatorin; and (3) selecting a compound that reduces the binding compared to binding of the antibody to mouse equatorin or human equatorin without contacting with a test compound. The antibody can have an effect of inhibiting fertilization. The antibody can be an antibody that recognizes the region of mouse equatorin. The mouse equatorin or the human equatorin can be expressed in cultured cells. The mouse equatorin can be a partial peptide of mouse equatorin that comprises sequential amino acid residues from position 101 to position 146 of the amino acid sequence of SEQ ID NO: 2 or SEQ ID NO: 3 and contains an O-glycosylated threonine residue located at position 138 of the amino acid sequence of SEQ ID NO: 2 or SEQ ID NO: 3. The human equatorin can be a partial peptide of human equatorin that comprises sequential amino acid residues from position 92 to position 144 of the amino acid sequence of SEQ ID NO: 5 and contains an O-glycosylated threonine residue located at position 136 of the amino acid sequence of SEQ ID NO: 5. The method can further comprise contacting a selected compound with male germ cells, detecting fertilization between the male germ cells and female germ cells, and selecting a compound that inhibits the fertilization.

The present inventors cloned the equatorin gene and found it to encode a highly glycosylated protein, as shown in FIGS. 1-4. With regard to the biochemical nature of equatorin, since equatorin is a highly glycosylated sialoglycoprotein in mature sperm, it could not be detected by SYPRO Ruby (FIG. 1B, lanes 3 and 4) or silver staining (data not shown). By contrast, the equatorin band became detectable by Pro-Q Emerald 300 staining (FIG. 2, lane 6), demonstrating sufficient staining intensity for its excision for LC-MS/MS analysis. This lack of detection of equatorin using traditional protein staining protocols is attributable to the abundant carbohydrates, including sialic acid moieties, that interfere with the staining of glycoproteins in these protocols. In fact, desialylated equatorin was detected by silver staining (data not shown). Other glycoproteins have also been reported to show poor detectability with standard gel stains such as silver stain and Coomassie Brilliant Blue staining, including flagellasialin [40].

Based on sequence alignment analysis of equatorin homologues, the long form-specific region is highly conserved in mammals. No data are currently available to confirm that the long form is a precursor of the short form of equatorin. It is unclear why or how the long and short forms are present in the testis or which form is translated.

The results from the glycosylation study of equatorin, described below with reference to FIG. 4B, indicate that the asialylated form is estimated to be 27 kDa (FIG. 4B), while the sialylated form is estimated to be at least 40 kDa (FIG. 1). Considering the fact that neuraminidase treatment reduced the relative molecular mass by roughly 13 kDa, equatorin is expected to be highly sialylated or polysialylated, although we cannot completely rule out the possibility that the reduction is due to either protein cleavage induced by loss of stability [41, 42] or intrinsic proteases activated by neuraminidase treatment.

With regard to the MN9 epitope, it is unlikely that it contains N-linked carbohydrate moieties, since the MN9 antibody still detected the equatorin molecule following PNGase treatment, (as described below with reference to FIG. 4B), which is known to release N-linked carbohydrates [43]. In addition, it is also unlikely that a neuraminic acid residue is essential for the MN9 epitope, since equatorin could be detected following neuraminidasetreatment (FIG. 4B). Neuraminidase from *Arthrobacter ureafaciens* is known to release α2-(3,6,8)-linked neuraminic acid residues [44]. With regard to the possibility of phosphorylation, MN9 antigenicity of sperm equatorin remained even after CIAP treatment (FIG. 4A), indicating that the MN9 epitope is not phosphorylated. For possibility of O-glycosylation, the MN9 epitope was sensitive to the O-glycosylation inhibitor Benzyl-α-GalNAc (FIG. 4C), suggesting that O-glycosylation is involved in the MN9 epitope. In addition, the finding that MN9 antibody detectability was lost by the substitution of threonine 138 to alanine (FIG. 5C) indicates that the MN9 epitope region is localized around threonine138. Taken together, these data strongly suggest that the MN9 epitope contains an O-glycosylation around threonine 138 or that the modification is at least necessary for the equatorin conformation that the MN9 antibody can recognize. It is noteworthy that the threonine corresponding to threonine 138 of mouse equatorin is well conserved in many mammals, including humans. In this context, further analyses are required to reveal the structure around threonine 138, including the glycan structure. With regard to the domain of equatorin responsible for sperm-egg interaction, the anti-EQ$_{70-83}$ peptide antibody did not inhibit sperm-egg interaction (data not shown), suggesting the importance of the MN9 epitope domain around threonine 138.

Figure 5:
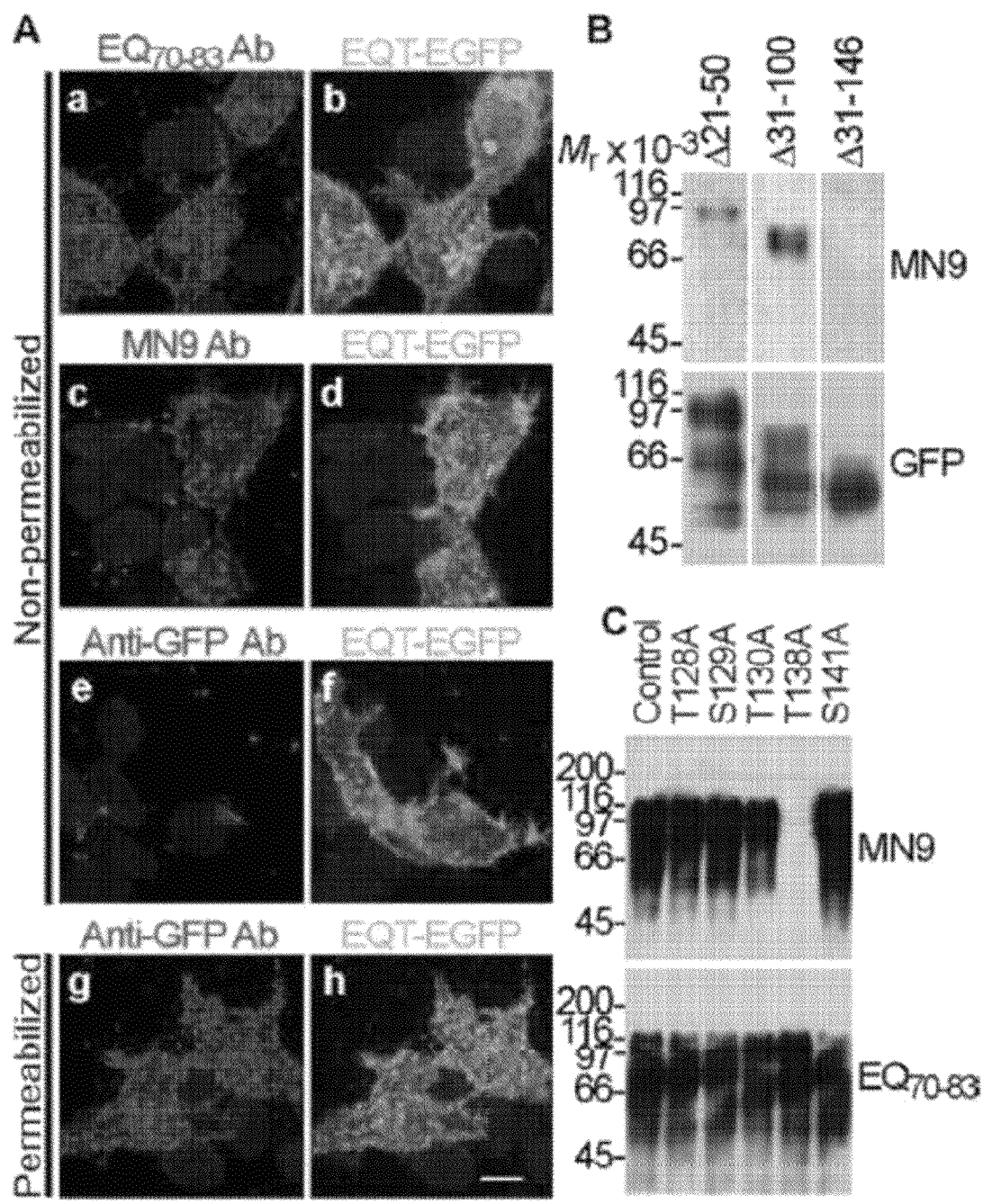
FIG. 5A. Orientation of the equatorin epitope on HEK293T cell plasma membrane.
FIG. 5B. Partial deletion of EGFP-tagged equatorin EQT (L)-EGFP; e.g., Δ21-50 indicates deletion of 21-50 amino acid sequence. Western blot (12.5% gel) by MN9 antibody (upper panel) and anti-GFP antibody (lower panel; positive control).
FIG. 5C. Single amino acid substitution mutants of EGFP-tagged equatorin, e.g., T128A indicates the substitution of 128th aa T (threonine) to A (alanine). Western blot (12.5% gel) with MN9 antibody (upper panel) and $EQ_{70-83}$ antibody (lower panel; positive control).
Figure 6:
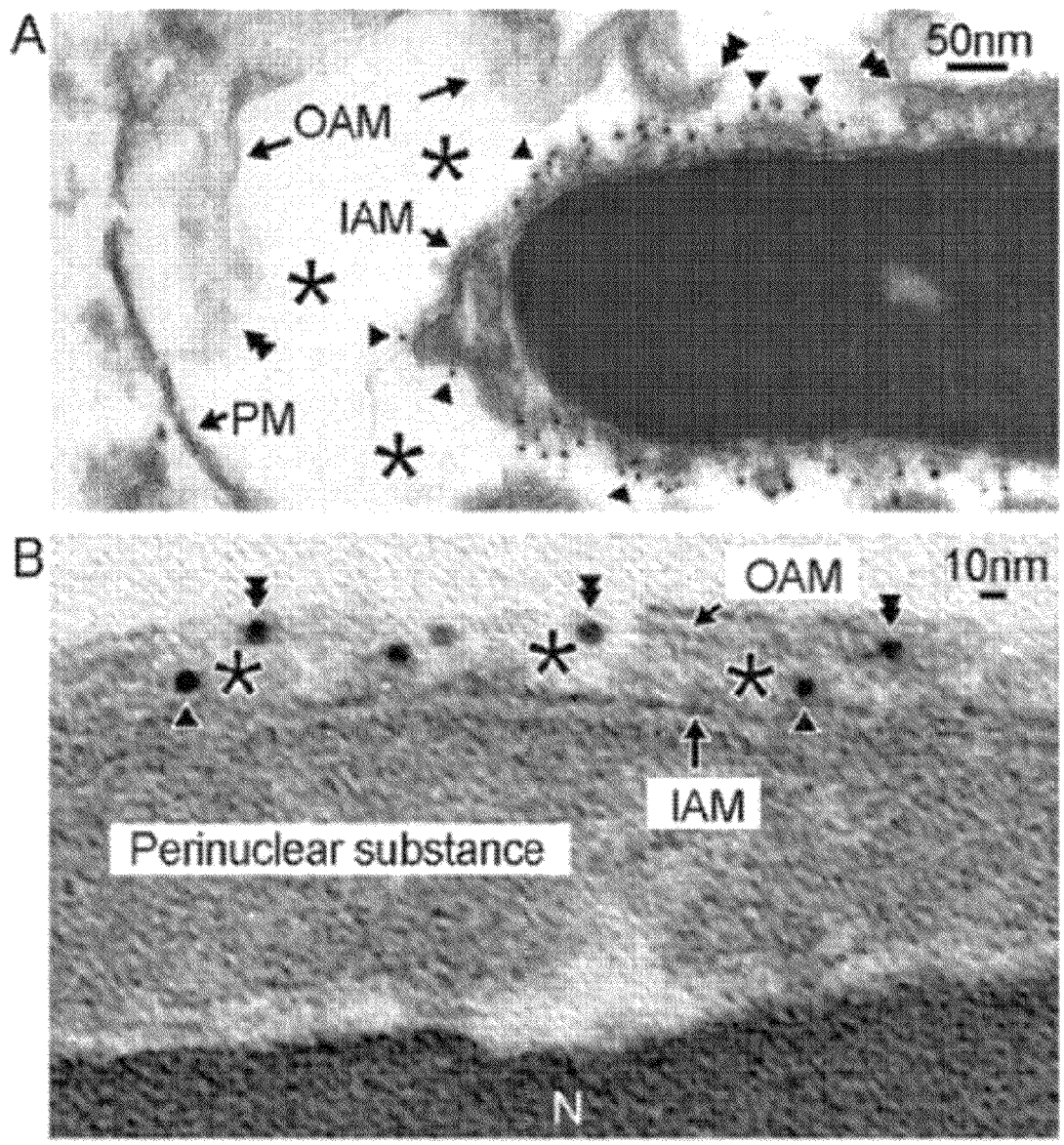
FIGS. 6 A and B. Localization of equatorin in mature sperm by immunogold electron microscopy using MN9 antibody.
Figure 7:
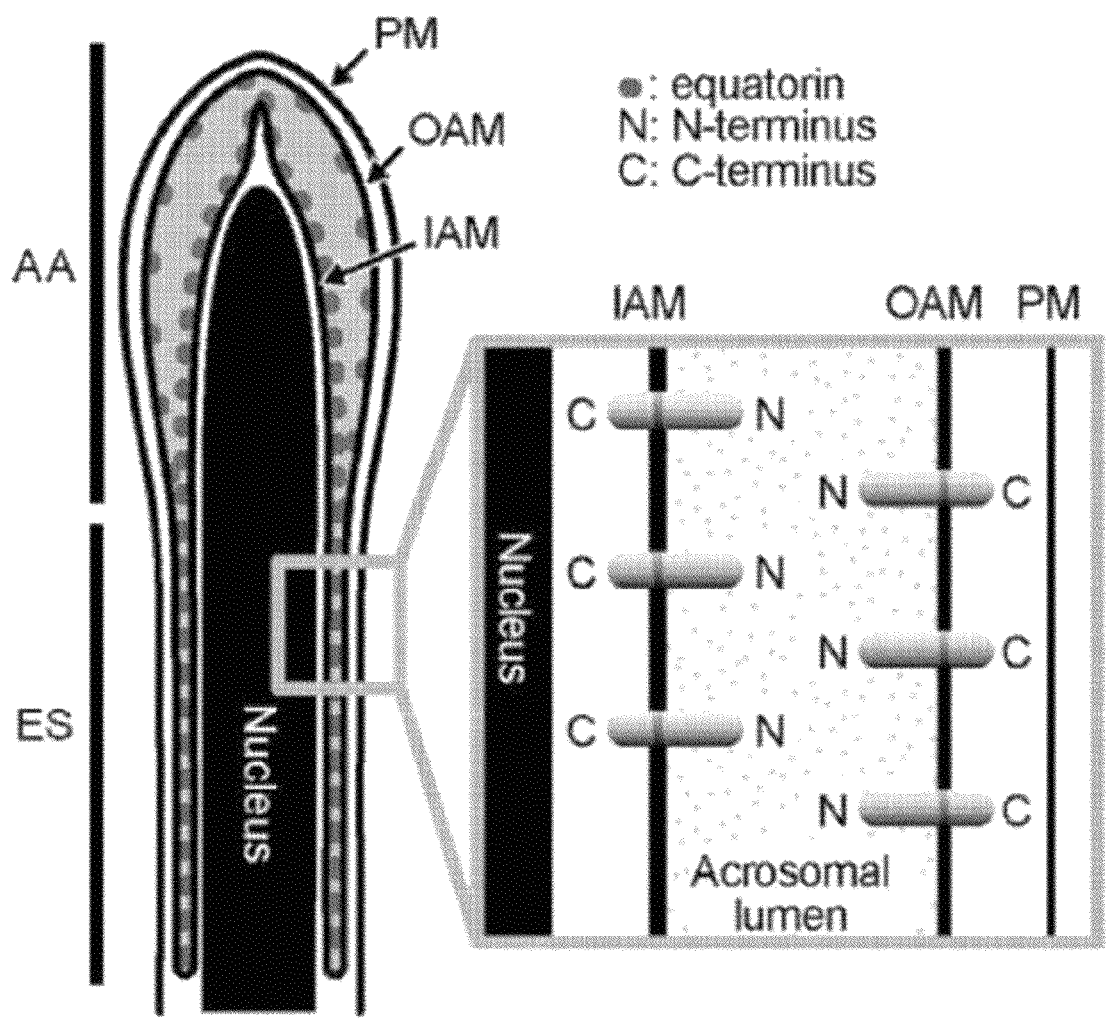
FIG. 7. Schematic drawing of sperm head to show the localization of equatorin in acrosome.

The results, described below, derived from the EGFP-tagged equatorin study in HEK293T cells (FIG. 5) and immunogold staining analysis (FIG. 6) indicate that equatorin is predominantly present in the inner acrosome membrane, with the N-terminus facing the acrosomal lumen, as shown in FIG. 7. Before the acrosome reaction, equatorin was never found on the sperm plasma membrane, as previously reported [11, 12, 23]. During the acrosome reaction, some equatorin was released from the acrosome and reached the plasma membrane over the equatorial segment, where sperm-egg fusion takes place [11, 12, 23]. There appear to be no reports showing the detailed orientation of the acrosomal transmembrane protein that is translocated during the acrosome reaction. Some acrosomal proteins such as Izumol and SPACA4 have also been reported to translocate to the sperm cell surface.

In summary, equatorin is a 40-50 kDa type 1 transmembrane N,O-sialoglycoprotein, composed of a putative signal peptide region in the N-terminal 20 aa and a transmembrane region at residues 186-208. The gamete interaction-inhibiting epitope recognized by the MN9 antibody requires post-translational modification, most likely O-glycosylation on threonine 138. The evidence accumulated thus far suggests that the N-terminal side of equatorin bears the MN9 epitope and faces the acrosomal lumen (FIG. 7). During the acrosome reaction, some equatorin on the acrosomal membranes translocates onto the surface of the plasma membrane over the equatorial segment, and equatorin on the inner acrosomal membrane becomes exposed. The domain of equatorin around threonine 138 that reaches the equatorial segment can play a role in sperm-egg interaction.

The present invention will be further clarified by the following examples, which are intended to be exemplary of the present invention.

EXAMPLES

Indirect Immunofluorescence (IIF) Image for Human Sperm

For IIF with MN9 antibody, human ejaculated sperm were rinsed with culture grade medium (commercially available) and treated with 0.1% Triton X-100 in phosphate buffered saline (PBS) for 30 min. Then, the sperm were treated with MN9 antibody at a dilution of 1/20,000 at 4° C. overnight. After the treatment, the sperm were rinsed with PBS several times and sequentially incubated with Alexa Fluor 488 goat anti-mouse IgG (H+L) (0.5 µg/ml) at room temperature for 1 h. After rinsing with PBS, observation was performed with Olympus BX50 microscope using oil-immersed UPlanApo 100 objective lens (Olympus Co., Tokyo, Japan) equipped with an imaging system composed of appropriate filters for fluorescence and a CCD camera RETIGA Exi FAST 1394 (Qimaging, Surrey, BC, Canada). Acquisition and storage of the data were controlled by SlideBook 4 software (Intelligent Imaging Innovations, Denver, Colo., USA).

Western Blot for Human Sperm

Human ejaculated sperm recovered by masturbation after three days abstinence were rinsed with phosphate buffered saline (PBS) and homogenized in SDS sample buffer (50 mM Tris-HCl [pH 6.8], 2% SDS [w/v], 10% [v/v] glycerol, 0.002% [w/v] bromophenol blue). After the samples were boiled at 98° C. for 10 min just before loading, insoluble constituents were removed by centrifugation at 16,000 g for 10 min. The isolated supernatant ($2.5 \times 10^6$ sperm/lane) was loaded and separated in 12.5% gel by sodium dodecyl sulfate polyacrylamide gel electrophoresis (SDS-PAGE). The separated proteins were blotted onto a polyvinylidene difluoride membrane (Millipore, Bedford, Mass., USA). The membranes were soaked in 5% (w/v) skim milk in TBS-T (20 mM Tris-HCl [pH 7.6], 137 mM NaCl, 0.1% [w/v] Tween 20) for 60 min to suppress the background and treated with MN9 antibody (at a dilution of 1/4000) at room temperature for 60 min. After rinsing with TBS-T, the membrane was treated with horseradish peroxidase HRP conjugated sheep anti-mouse IgG antibody (at a dilution of 1/10000) for 60 min. After the membrane was rinsed with TBS-T, the reacted proteins were visualized using ECL Plus Western Blotting Detection System (GE Healthcare) and exposed to X-ray films.

Materials and Methods

Animals and Reagents

Male ICR mice (16 weeks old) were purchased from Charles River Japan (Yokohama, Japan) and kept in an air-conditioned room (12 hours light/dark cycles, 24° C.) with free access to food and water. This study was conducted according to the guidelines for the care and use of laboratory animals of the Chiba University Graduate School of Medicine.

A monoclonal antibody, MN9 (IgG2a), which specifically recognizes equatorin, was produced in female BALB/c mice by immunizing them with cauda epididymal sperm from CD1 mice. Antibody production, purification, and characterization were previously reported [11, 12, 23, 24]. The $EQ_{70-83}$ antibody is a specific antibody newly raised against 14-amino acids (aa) of equatorin from residue 70 to 83 as described below.

General chemicals and antibodies used were as follows: HRP-conjugated sheep anti-mouse IgG, HRP-conjugated donkey anti-rabbit IgG, PY20 mouse anti-phosphotyrosine monoclonal antibody (GE Healthcare; Little Chalfont, Buckinghamshire, UK); Pro-Q Emerald 300 glycoprotein gel staining kit, SYPRO Ruby protein gel stain, rabbit anti-GFP antibody IgG fraction, Alexa Fluor 488 goat anti-mouse IgG, Alexa Fluor 546 goat anti-rabbit IgG, Alexa Fluor 555 donkey anti-mouse IgG, Alexa Fluor 568 goat anti-rabbit IgG (Invitrogen, Carlsbad, Calif., USA); Hoechst 33258 and O-glycosylation inhibitor benzyl-2-acetamido-2-deoxy-α-D-galactopyranoside (Benzyl-α-GalNAc) [29] (Sigma Aldrich; St. Louis, Mo., USA); and 5 and 10 nm colloidal gold-conjugated anti-mouse IgG (BBInternational, Cardiff, UK). Total RNA was extracted using an RNeasy protect Mini Kit (Qiagen Sciences, Germantown, Md., USA). We synthesized cDNA by oligo(dt) priming using a Transcriptor First Strand cDNA Synthesis Kit (Roche Diagnostics, Mannheim, Germany). PNGase F, Calf intestinal alkaline phosphatase (CIAP) (New England Biolabs, Beverly, Mass., USA) and neuraminidase (*Arthrobacter ureafaciens*; Marukin Bio, Kyoto, Japan) were used according to the manufacturer's instructions.

Western Blot Analysis

Western blot analysis was used to examine the distribution of equatorin in various tissues and to verify the expression of recombinant equatorin protein in HEK293T cells, dephosphorylation, deglycosylation, and amino acid substitution assays. The samples for these experiments were extracted with SDS sample buffer (50 mM Tris-HCl [pH 6.8], 2% SDS, 100 mM DTT, 10% [v/v] glycerol, 0.002% [w/v] Bromophenol blue). The lysates were heated for 10 minutes at 98° C. and centrifuged at 16,000 g for 10 minutes to remove insoluble material. The lysates were then separated by sodium dodecyl sulfate polyacrylamide gel electrophoresis (SDS-PAGE) and blotted onto a polyvinylidene difluoride membrane (PVDF; Millipore, Bedford, Mass., USA). Western blot analysis was performed according to a standard protocol using TBS-T (20 mM Tris-HCl [pH 7.6], 137 mM NaCl, 0.1% [w/v] Tween 20) containing 5% (w/v) skimmed milk a as blocking solution and for antibody dilution. Antibody concentrations used for Western blot analysis were as follows: MN9 antibody at 1:4,000 (ca, 0.1 µg/ml), $EQ_{70-83}$ antibody at 0.3 µg/ml, anti-GFP antibody at 1 µg/ml, and HRP conjugated secondary antibodies at 1:10,000. The blots were developed with ECL Plus Western Blotting Detection Reagents (GE Healthcare) and exposed to X-ray film.

Sample Preparation for Mass Spectrometry Analysis

Sperm ($1.3 \times 10^9$) were removed from cauda epididymides and washed twice in phosphate buffered saline (PBS). The sperm were then suspended in 0.1% Triton X-100 in PBS with Complete protease inhibitors (Roche Diagnostics) and kept on ice for 10 minutes, then centrifuged at 290 g for 10 minutes. The precipitated sperm were extracted with SDS-EDTA solution (75 mM NaCl, 1% SDS, 25 mM EDTA, [pH 6.0]) containing Complete protease inhibitors and centrifuged at 16,000 g for 10 minutes to remove insoluble debris. Liver was directly extracted with SDS-EDTA solution as a negative control. SDS-EDTA solution extracts were precipitated with a 2D clean-up kit (GE Healthcare). The precipitated proteins were resuspended in NP-40 lysis buffer (150 mM NaCl, 1% NP-40, 50 mM Tris-HCl [pH 8.0]). The lysates were pre-cleared with protein G sepharose (GE Healthcare) for an hour at 4° C. and incubated with 10 μg of MN9 antibody overnight at 4° C. Protein G sepharose beads were added and incubated for an hour at 4° C. The beads were washed three times with NP-40 lysis buffer and once with 50 mM Tris-HCl (pH 8.0). The beads were then suspended in SDS sample buffer and heated for 5 minutes at 98° C. to dissociate precipitates. After separation by SDS-PAGE, samples were detected using Pro-Q Emerald 300, SYPRO Ruby, and Western blot analysis with the MN9 antibody. The bands of interest were excised from a Pro-Q Emerald 300-stained gel. In-gel trypsin digestion and LC-MS/MS analysis were performed as previously reported [30].

Alignment Analysis

A homologue search was done using the PSI-BLAST program [31], and sequence alignment was achieved using the T-Coffee server [32, 33]. The signal peptide region was predicted using the SignalIP3.0 server [34, 35]. The transmembrane domain was predicted using the TMHMM 2.0 server [36, 37].

Antibody Production

Figure 9:
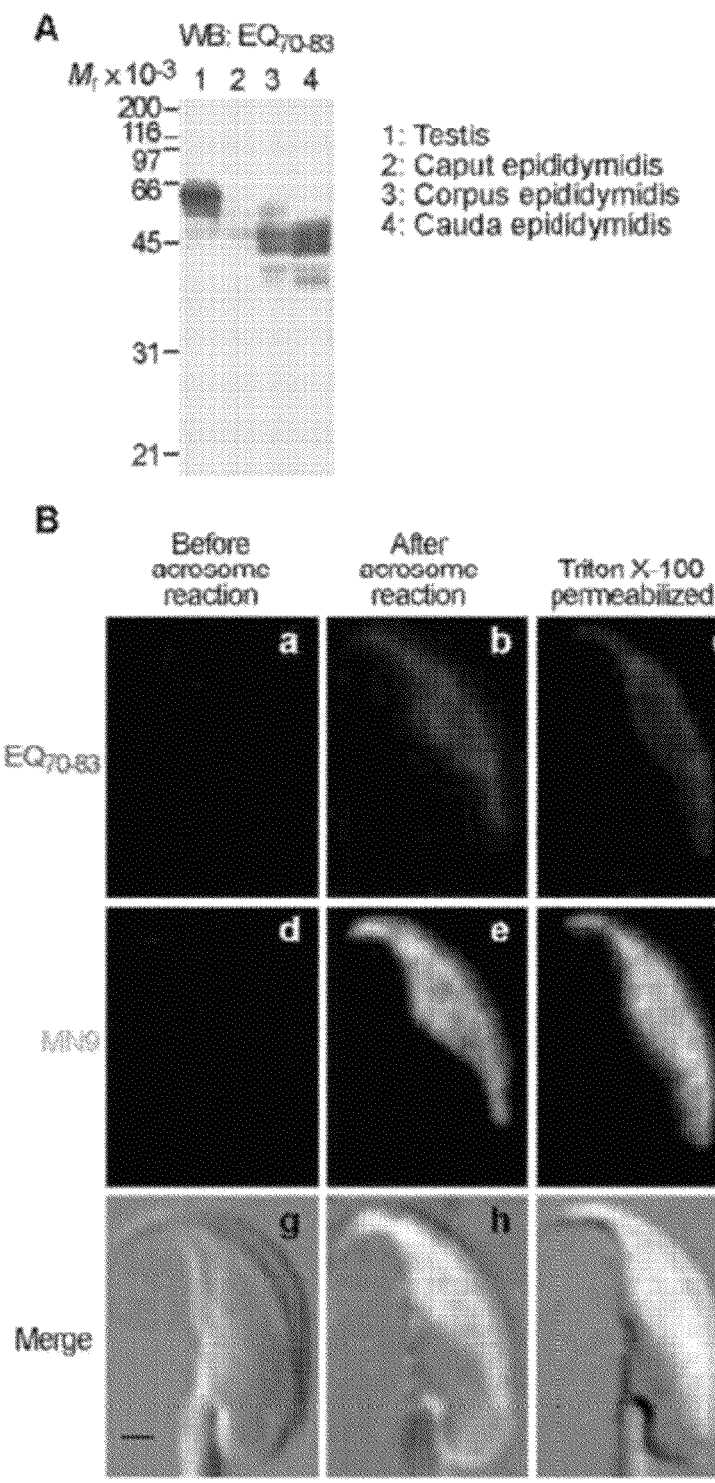
FIG. 9A. Western blot (12.5% gel) analysis with $EQ_{70-83}$ antibody.
FIG. 9B. IIF microscopy of cauda epididymal sperm with $EQ_{70-83}$ and MN9 antibodies.

Following the identification of equatorin as described in the Results section, an anti-equatorin polyclonal antibody was produced and termed the EQ70-83 antibody. Briefly, a rabbit was immunized with a synthetic 14-residue partial sequence of equatorin (GNYYKDIKQYVFTT (SEQ ID NO: 6)) conjugated to the keyhole limpet hemocyanin. The $EQ_{70\text{-}83}$ antibody was then affinity purified using beads conjugated with the synthetic 14-residue peptide and adjusted to the final concentration of 1.2 mg/ml. Since the $EQ_{70\text{-}83}$ and MN9 antibodies showed a similar staining pattern on Western blot and immunofluorescence (FIG. 9), the $EQ_{70\text{-}83}$ antibody was considered to be verified as anti-equatorin antibody and used in this study.

RT-PCR Analysis

To examine the expression of equatorin mRNA in various tissues, RT-PCR was performed. The specific primer pairs used were as follows: Eqt-forward (5'-AATGCTGGG-GATCTCGCTGATG-3' (SEQ ID NO: 7)) and Eqt-reverse (5'-ATTACTCGGTGATCCTTCCTTGTTC-3' (SEQ ID NO: 8)); Gapdh-forward (5'-ACCACAGTCCATGCCATCAC-3' (SEQ ID NO: 9)) and Gapdh-reverse (5'-TCCACCACCCT-GTTGCTGTA-3' (SEQ ID NO: 10)) were used as controls. Nucleotides from 550 to 1011 of the equatorin long form were partially amplified. There were 25 cycles of amplification: denaturation for 30 seconds at 94° C., annealing for 30 seconds at 60° C., and elongation for 30 seconds at 72° C.

Production of Recombinant Protein

HEK293T cells were purchased from the Riken Cell Bank (Japan) and cultured in Dulbecco's modified Eagle's medium with 10% fetal bovine serum, 100 units/ml penicillin, and 100 μg/ml streptomycin at 37° C. with 5% $CO_2$ in air. Vectors were transfected using the FuGENE HD transfection reagent (Roche Diagnostics) as described in the manufacture's manual. Briefly, cells were cultured for 24 hours after transfection (48 hours for the amino acid substitution study to obtain a high concentration) and cells washed with PBS were solubilized in SDS sample buffer for Western blot analyses. The vector constructs are described in the vector construction section.

Indirect Immunofluorescence (IIF) Microscopy for Testes and Epididymides

To examine the expression of equatorin in detail, IIF microscopy was performed with the MN9 and $EQ_{70\text{-}83}$ antibodies. Male ICR mice were anesthetized with Nembutal (Abbott Laboratories, Abbott Park, 140 IL, USA) and fixed with Bouin's solution by perfusion through the left ventricle. Testes and epididymides were removed and immersed in the same fixative for an hour. After being dehydrated in graded ethanol series and xylene, the samples were processed for paraffin embedding and sectioned at 2.5 μm thickness. The sections were deparaffinized and autoclaved for 5 minutes at 120° C. to activate the antigenicity. After 30 minutes in 0.1% Triton X-100 in PBS, nonspecific antibody binding was suppressed by incubation in blocking buffer (PBS containing 5% normal goat serum and 3% bovine serum albumin) for 30 minutes at room temperature. The sections were then incubated overnight with MN9 antibody (1:20,000 dilution, ca, 0.02 μg/ml) and $EQ_{70\text{-}83}$ antibody (0.6 μg/ml) at 4° C. and rinsed in PBS. The sections were then incubated with Alexa Fluor 488 goat anti-mouse IgG (0.5 μg/ml), Alexa Fluor 546 goat anti-rabbit IgG (0.5 μg/ml) and Hoechst 33258 (5 μg/ml) for one hour at room temperature. Observations were made using an Olympus BX50 (Olympus Co., Tokyo, Japan) microscope with a UPlanApo 40×NA 0.85 dry objective lens equipped with an imaging system composed of appropriate filters for fluorescence and a RETIGA Exi FAST 1394 CCD camera (Qimaging, Surrey, BC, Canada). Data acquisition and storage were controlled with SlideBook 4 software (Intelligent Imaging Innovations, Denver, Colo., USA).

Dephosphorylation of Equatorin by Calf Intestinal Alkaline Phosphatase (CIAP)

Sperm removed from cauda epididymides were washed with PBS, extracted with SDS sample buffer, subjected to SDS-PAGE and blotted onto a PVDF membrane. The PVDF membrane was incubated in NEB buffer 3 (100 mM NaCl, 50 mM Tris-HCl, 10 mM MgCl, 2 mM DTT [pH 7.9], EDTA-free Complete mini protease inhibitors) with CIAP (20 U/ml) for one hour at 37° C., and the membrane was then subjected to immunostaining with the MN9 antibody to check the phosphorylation status of MN9 epitope or with the PY20 anti-phosphotyrosine antibody (0.1 μg/ml) as a control to confirm dephosphorylation by CIAP treatment. Control (non-dephosphorylated) samples were incubated without CIAP. TBS-T containing 1% (w/v) bovine serum albumin was used for blocking solution.

PNGase F and Neuraminidase Treatment

Glycosidase treatments were performed basically according to the manufacturer's instructions (New England Biolabs) with slight modification: neuraminidase was simultaneously added to the PNGase F treatment protocol. Sperm were removed from cauda epididymides ($5\times10^5$ sperm suspended in 5 μl PBS/tube), washed with PBS, denatured and solubilized by adding 1 μl denaturing buffer (5% SDS, 0.4 M DTT) and heated for 10 minutes at 98° C. The samples were then neutralized by adding 2 μl of G7 buffer (0.5 M sodium phosphate, pH 7.5) and 2 μl of 10% NP-40 and centrifuged at 16,000 g to remove insoluble materials. Protease activity in the recovered supernatant was suppressed by adding Complete protease inhibitors and 1 μg/ml of pepstatin (Roche Diagnostics). PNGase F (125 U) or neuraminidase from *Arthrobacter ureafaciens* (0.05 U), or both were added to the supernatant and incubated for 12 hours at 37° C. The samples were then mixed with equal volumes of SDS sample buffer and subjected to Western blot analysis. The control samples were incubated without these glycosidases.

Inhibition of O-glycosylation on Equatorin by Benzyl-α-Gal-NAc

HEK293T cells were supplemented with 0, 2 and 4 mM Benzyl-α-GalNAc prior to transfection of the pKSCX-Eqt (L)-EGFP vector. The cells were cultured for at least 24 hours in the presence of Benzyl-α-GalNAc, then solubilized in SDS sample buffer and subjected to Western blot analyses. Densitometry analysis of the immunoblots was done using ImageJ software (http://rsb.info.nih.gov/ij/index.html). The relative ratio of the immunostaining intensity of the MN9 antibody to that of the $EQ_{70-83}$ antibody ($MN9/EQ_{70-83}$) at 0 mM Benzyl-α-GalNAc was regarded as 1. The relative ratios of $MN9/EQ_{70-83}$ at 2 and 4 mM Benzyl-α-GalNAc were then calculated. The results are shown in a bar graph. The vector construct is described in the vector construction section.

Determination of the Orientation of the Equatorin Epitope Region in the HEK293T Cell Plasma Membrane In order to identify the MN9 epitope, the orientation of equatorin in the cell membrane was examined in HEK293T cells. Cells were cultured on a glass bottom dish (AGC Techno Glass Co., Ltd. Chiba, Japan) precoated with polyethyleneimine (Sigma Aldrich) and transfected with a C-terminally EGFP-tagged equatorin vector termed pKSCX-Eqt (L)-EGFP. The cells were cultured at least 24 hours after the transfection and washed once with PBS. Thereafter, cells were fixed with 4% paraformaldehyde (PFA) in PBS for 30 minutes. After washing twice in PBS, cells were incubated in PBS or permeabilized with 0.1% Triton X-100 for 10 minutes and then incubated with the MN9 antibody (1:40,000 dilution, ca, 0.01 μg/ml), the $EQ_{70-83}$ antibody (0.24 μg/ml), or an anti-GFP antibody (2 μg/ml) for one hour at room temperature and rinsed with PBS. Cells were then incubated with Alexa Fluor 555 donkey anti-mouse IgG (0.5 μg/ml) or Alexa Fluor 568 goat anti-rabbit IgG (0.5 μg/ml) and Hoechst 33258 (5 μg/ml) in PBS for one hour at room temperature. Cells were analyzed using an Olympus IX 71 (Olympus) microscope with a UPLSAPO 60×NA 1.2 water immersion objective lens equipped with a CSU-XI confocal scanner (Yokogawa Electric Corporation, Tokyo, Japan). 3D projection images were captured using a QuantEM 512SC CCD camera (Photometrics, Tucson, Ariz., USA) controlled by SlideBook 4 software.

Immunogold Electron Microscopy

After washing twice in TYH (Toyoda, Yoshida and Hoshi) medium [38], cauda epididymal sperm were frozen once at −80° C. and thawed before applying the primary antibody to permeabilize the membrane. The MN9 antibody was applied to the sperm for one hour. The sperm were then incubated in a solution of colloidal gold-conjugated anti-mouse IgG (ca, 1 μg/ml) for one hour. After rinsing in the medium, sperm were fixed in 1% glutaraldehyde and postfixed in 2% osmium tetroxide solution. The fixed sperm were embedded in 2% agar, routinely dehydrated in an ethanol series and embedded in Epon 812 (TAAB Laboratories Equipment, Berks, UK). Ultrathin sections were routinely made using an ultramicrotome (Ultracut E; Reichert-Jung, Wien, Austria) and stained with lead and uranyl acetate for observation with a transmission electron microscope (JEM-1200 EX; JEOL, Tokyo, Japan).

Vector Construction for Mouse Recombinant Equatorin

The FANTOM FLS clone (ID: 1700028B15 relevant to cloned mouse equatorin long form) was purchased from DNAFORM (Kanagawa, Japan). The equatorin long form was inserted into pET-23a (Novagen, Madison, Wis., USA) in frame with a C-terminal 6×His-tag, designated as pET-23a-Eqt(L)-His, and used for *E. coli* protein expression. The pET-23a-Eqt(L)-His vector was digested with BamHI and Bpu1102I. Fragments were blunt-ended by the Bunting high (Toyobo co., Ltd., Osaka, Japan) and ligated into pKSCX-IRES-EGFP, which digested with EcoRV and treated with CIAP. This plasmid was named pKSCX-Eqt(L)-His and used for mammalian cell culture. An EGFP-tagged equatorin protein expression vector pKSCX-Eqt(L)-EGFP was created by deleting the His-tag and IRES with an inverse PCR mutagenesis method using the KOD Plus mutagenesis kit (Toyobo) starting from pKSCX-Eqt(L)-His according to the manufacturer's instructions using the appropriate primers (Table 1). Vectors for the equatorin short form and equatorin mutant protein expression (partial deletion and single amino acid substitution) were also created using PCR-based mutagenesis (Table 1). All vectors were verified by DNA sequencing.

TABLE 1

Primer pairs used in PCR mutagenesis for vector construction.

| product | Template vector | primers | | SEQ ID NO |
|---|---|---|---|---|
| pKSCX-Eqt-EGFP | pKSCX-Eqt-His | Forward | 5'-CCCCGCGTCGACGTAATTACTCGGTGATCC-3' | 11 |
| | | Reverse | 5'-CGCGGATCCATGGATTTTATACTGTTGATC-3' | 12 |
| pKSCX-Eqt | pKSCX-Eqt-His | Forward | 5'-TGAGATCCGGCTGCTAACAAAGC-3' | 13 |
| | | Reverse | 5'-ATTACTCGGTGATCCTTCCTTGTTCAAC-3' | 14 |
| Eqt short | Eqt long | Forward | 5'-GCTCCAATCAAACAGTCTTAACCG-3' | 15 |
| | | Reverse | 5'-CTTCTGTTGGATGGAAGTAAGATAG-3' | 16 |
| EqtΔ21-50 | pKSCX-Eqt-EGFP | Forward | 5'-GTTGCTTTACATAAATTGGAAGAG-3' | 17 |
| | | Reverse | 5'-TAGACTGATAATGTCTGGGAGGAAAACCC-3' | 18 |
| EqtΔ31-100 | pKSCX-Eqt-EGFP | Forward | 5'-TTTGCTGTGAAGAAGAACTATAAAGCC-3' | 19 |
| | | Reverse | 5'-CACACCAGCCTCCTGTCCCACAATG-3' | 20 |
| EqtΔ31-146 | pKSCX-Eqt-EGFP | Forward | 5'-ACAGCAGTGAGCATGGATGATAAAGAT-3' | 21 |
| | | Reverse | 5'-CACACCAGCCTCCTGTCCCACAATG-3' | 22 |
| Eqt(T128A) | pKSCX-Eqt-EGFP | Forward | 5'-CTCTCGTAAAGCCTCAACCCCCAATATACC-3' | 23 |
| | | Reverse | 5'-GGTATATTGGGGGTTGAGGCTTTACGAGAG-3' | 24 |
| Eqt(S129A) | pKSCX-Eqt-EGFP | Forward | 5'-CTCTCGTAAAACCGCAACCCCCAATATACC-3' | 25 |
| | | Reverse | 5'-GGTATATTGGGGGTTGCGGTTTTACGAGAG-3' | 26 |

TABLE 1-continued

Primer pairs used in PCR mutagenesis for vector construction.

| product | Template vector | primers | | SEQ ID NO |
|---|---|---|---|---|
| Eqt(T130A) | pKSCX-Eqt-EGFP | Forward | 5'-CTCTCGTAAAACCTCAGCCCCAATATACC-3' | 27 |
| | | Reverse | 5'-GGTATATTGGGGGCTGAGGTTTTACGAGAG-3' | 28 |
| Eqt(T138A) | pKSCX-Eqt-EGFP | Forward | 5'-CCTGCATTTTGGGCAATATTATCTAAAGC-3' | 29 |
| | | Reverse | 5'-GCTTTAGATAATATTGCCCAAAATGCAGG-3' | 30 |
| Eqt(S141A) | pKSCX-Eqt-EGFP | Forward | 5'-GCATTTTGGACAATATTAGCTAAAGCTG-3' | 31 |
| | | Reverse | 5'-CAGCTTTAGCTAATATTGTCCAAAATGC-3' | 32 |

Results

Distribution of Equatorin in Various Tissues

In order to determine the distribution of equatorin in various tissues, Western blot analysis was performed with the MN9 antibody. Solubilized proteins (20 μg/lane) were loaded. Tissue samples present in each lane were as follows: lane 1, cerebrum; lane 2, cerebellum; lane 3, heart; lane 4, lung; lane 5, liver; lane 6, pancreas; lane 7, spleen; lane 8, kidney; lane 9, bladder; lane 10, large intestine; lane 11, small intestine; lane 12, testis; lane 13, caput epididymidis; lane 14, corpus epididymidis; lane 15, cauda epididymidis. Among the tissues examined, equatorin bands ranging from 40 to 65 kDa in testes, as shown in FIG. 1A, lane 12, and epididymides, as shown in FIG. 1A, lanes 13-15, were found. No bands were detected in other tissues (FIG. 1A, lanes 1-11). Since no bands were detected by the MN9 antibody in liver samples (FIG. 1A, lane 5), liver was used as a negative control for immunoprecipitation for LC-MS/MS analysis.

Identification of Equatorin and Analysis of the Amino Acid Sequence

Figure 8:
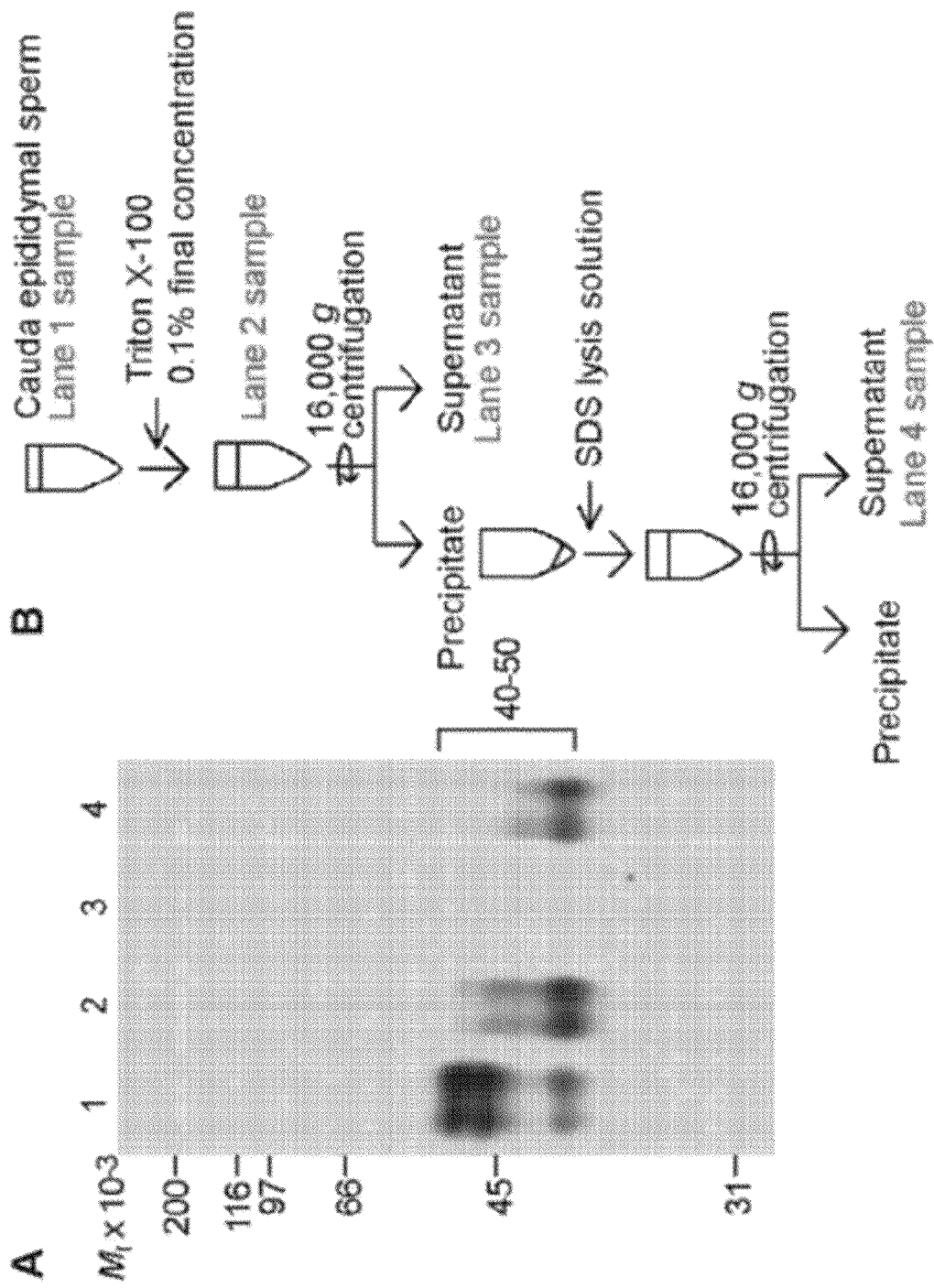
FIG. 8A Western blot analysis with MN9 antibody to detect solubilization, focusing of cauda sperm equatorin from 40-50 kDa to 40 kDa for LC-MS/MS.
FIG. 8B. Sample preparation diagram

Equatorin was purified by immunoprecipitation with the MN9 antibody. The same amounts of immunoprecipitates were loaded in each lane for SYPRO Ruby and Pro-Q Emerald 300 staining (lanes 3-6), while the 1/50 amount was loaded for Western blot (lanes 1 and 2). Tissue samples present in each lane were as follows: lanes 1, 3, and 5—liver (negative control); and lanes 2, 4, 6—cauda epididymal sperm. Lanes 1 and 2 were loaded with Western blot with MN9 antibody. In lanes 3 and 4, SYPRO Ruby staining was staining. In lanes 5 and 6, Pro-Q Emerald 300 staining was used. Equatorin focused on 40 kDa (lanes 2 and 6). Purified equatorin was identified as a 40 kDa band, as shown in FIG. 1B and FIG. 8. It is important to emphasize that equatorin, which was initially detected at 40 kDa by Western blot analysis (FIG. 1B, lane 2), could not be detected by conventional staining methods such as silver stain (unpublished data) or SYPRO Ruby (FIG. 1B, lane 4) but was detected by Pro-Q Emerald 300 staining (FIG. 1B, lane 6). No bands were detected in the control liver sample (FIG. 1B, lanes 1, 3 and 5).

The 40 kDa band expected to be equatorin was excised and subjected to LC-MS/MS analysis. Mascot search results indicated a single significant candidate 4930579C15Rik. Based on the FANTOM (Functional Annotation of Mouse) full-length cDNA database of RIKEN (http://fantom.gsc.riken-.go.jp), primers were designed for validation of the protein-coding region by sequencing cDNA prepared from the testes of an ICR mouse (GenBank/EMBL/DDBJ accession number AB438105 for the long form and AB438106 for the short form).

Figure 2:
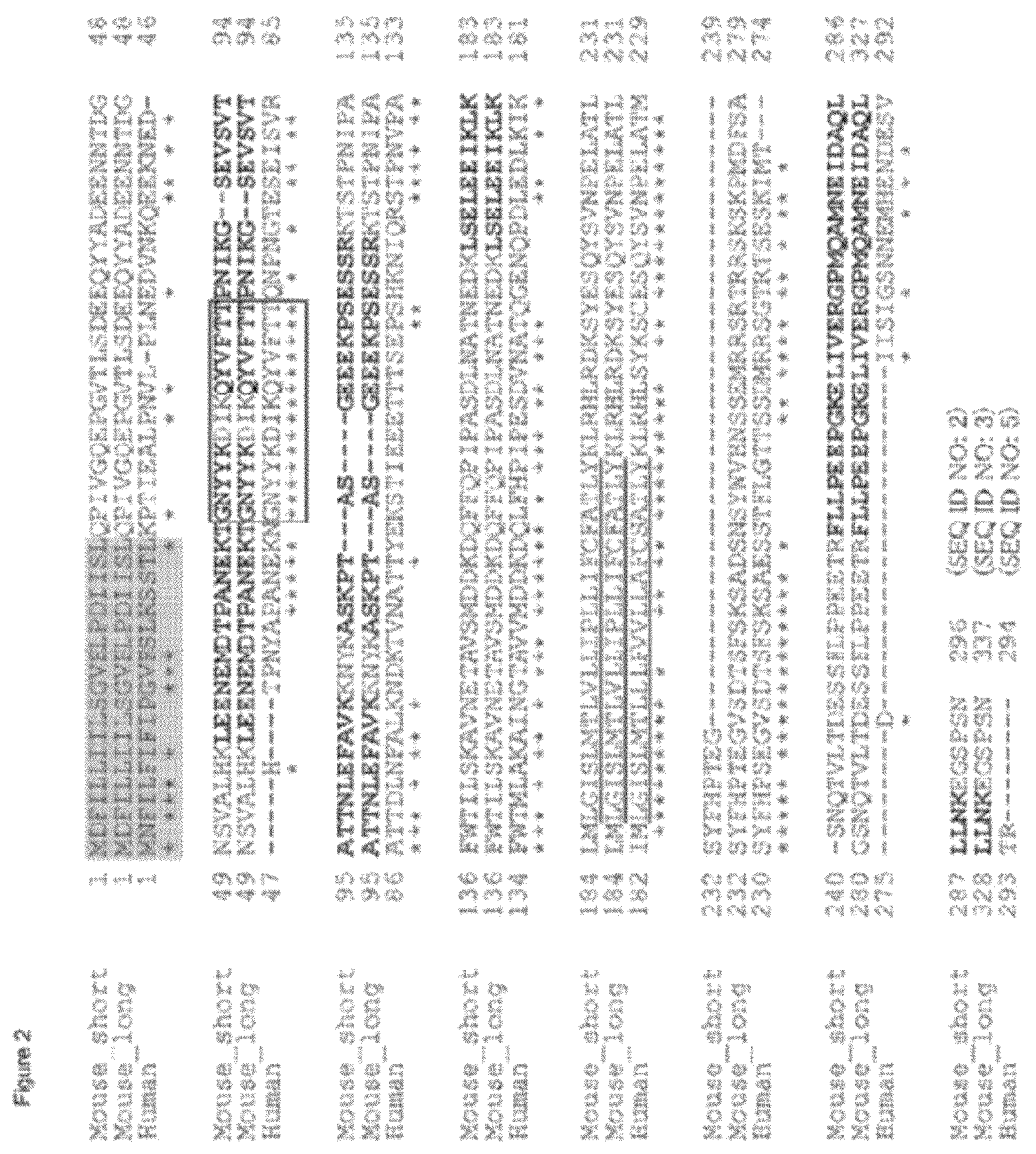

The data obtained were analyzed by amino acid sequence alignment for both human and mouse, based on a homologue search and domain search. The resulting peptide sequences are shown in FIG. 2. Identical sequences in the alignment are shown with asterisks. The peptide sequences detected by LC-MS/MS are shown in boldface letters. The 14-amino-acids sequence, boxed region, was used to raise $EQ_{70-83}$ antibody. The putative signal peptide region is shaded and the putative transmembrane domain is underscored. The molecular weight predicted from the amino acid sequence was 33,042 Da for short form (296 aa) and 37,764 Da for long form of equatorin (337 aa). There was a putative signal peptide region at the N-terminus at residues 1-20, and a transmembrane region at residues 186-208.

Based on the amino acid sequence alignment, oligopeptides ranging from residue 70 to 83, a highly conserved region in both humans and mice, were used to raise a specific antibody termed $EQ_{70-83}$, which was used for further experiments in this study.

Expression of Equatorin mRNA in Tissues

The expression of equatorin was investigated using recombinant protein in HEK293T cells. The mRNA expression of equatorin in various tissues was analyzed using RT-PCR. Interestingly, two bands, both long and short forms, were present in testes, as shown in FIG. 3A, lane 11. Tissue samples present in each lane were as follows: lane 1—cerebrum; lane 2—cerebellum; lane 3—heart; lane 4—lung; lane 5—liver; lane 6—spleen; lane 7—kidney; lane 8-, bladder; lane 9—large intestine; lane 10—small intestine; lane 11—testis; lane 12—caput epididymidis; lane 13—corpus epididymidis; lane 14—cauda epididymidis. No band was detected in other tissues, including epididymides (FIG. 3A, lanes 1-10 and 12-14).

Expression of Recombinant Equatorin in HEK293T Cells: the Verification Study

Verification of equatorin by recombinant protein was conducted in HEK293T cells. In order to verify the identity of equatorin, equatorin expression vectors were developed for long, short, EGFP-tagged long and EGFP-tagged short forms and these equatorin vectors were transfected into HEK293T cells and analyzed by Western blot (10% gel) using MN9 antibody. Same amounts of the cultured cell extracts were loaded in each lane. Expression vectors for short form (lane 1), long form (lane 2), EGFP-tagged short form (lane 3), and EGFP-tagged long form (lane 4). Short and long forms were found at 60-85 kDa (lanes 1 and 2), while EGFP-tagged short and long forms were found at 105 kDa (lanes 3 and 4). Both short and long forms were identified at 60 to 85 kDa (FIG. 3B, lanes 1 and 2), while both EGFP-tagged short and long forms were detected as much higher bands at approximately 105 kDa (FIG. 3B; lanes 3 and 4). Since the EGFP-tagged proteins were detected by the MN9 antibody as higher relative molecular mass bands than the untagged proteins, the cloned sequences were verified to be equatorin. The MN9 antibody did not 265 recognize equatorin proteins expressed in *E. coli* (data not shown).

Distribution of Equatorin in Testes and Epididymides

We then determined the distribution of equatorin in detail using indirect immunofluorescence (IIF) microscopy with $EQ_{70-83}$ and MN9 antibodies. The epitopes of these antibodies are different: the $EQ_{70-83}$ antibody recognizes a small peptide region from residue 70 to 83 of equatorin, while the MN9 antibody recognizes the antigenic region that undergoes post-translational modification (stated in the discussion). FIG. 3C shows distribution of equatorin in the testis and cauda epididymidis using IIF microscopy with $EQ_{70-83}$ antibody and MN9 antibody. Images a-c of FIG. 3C show testis. Images d-f of FIG. 3C show cauda epididymidis. Images a and d show $EQ_{70-83}$ antibody (represented in red when the figures are shown in color) as small dots dispersed in a circular fashion in image a and dispersed substantially around the asterisks in right and left edges of image d. Images b and e show MN9 antibody (represented in green when the images are shown in color) as small dots dispersed in a circular fashion in image b and substantially around the asterisks in image e. Images a, b, and c show counter staining with Hoechest 33258 (represented in blue when the images are shown in color) as small dots dispersed proximate the outer edges of the images. Merged images of $EQ_{70-83}$ antibody, MN9 antibody and differential interference contrast images are shown in FIG. 3C, images c and f. It should be noted that both $EQ_{70-83}$ antibody and MN9 antibody recognize acrosomal regions in developing spermatids (s7 and s16) of the seminiferous tubule at stage VII (VII; a-c) and in epidydimal sperm (asterisks; d-f), but these antibodies do not recognize epididymal epithelia (Ep; b-f). P; pachytene spermatocytes. s7 and s16; step 7 and step 16 spermatids, respectively. Bars=50 µm. Western blot analysis with the MN9 antibody detected recombinant equatorin. Thus, in agreement with the results of the Western blot study (FIG. 1A), IIF microscopy showed that equatorin detected by the $EQ_{70-83}$ and MN9 antibodies was present in both the testes and epididymides, showing the same staining pattern, but not in epididymal epithelial cells. The protein was sperm specific, including germ cells (FIG. 3C).

Phosphatase Treatment of Equatorin

Since it was found that the MN9 antibody did not recognize equatorin proteins expressed in *E. coli* during the verification studies, the MN9 epitope was thought to be post-translationally modified. The effect of dephosphorylation of the MN9 epitope was first examined using CIAP. FIG. 4A shows analysis of phosphorylation status of sperm equatorin by CIAP (phoshatase) treatment. Sperm proteins (12.5% gel SDS-PAGE; 5 µg/lane) on PVDF membranes were treated without (−) and with (+) CIAP and immunostained with MN9 antibody (upper panel) or with PY20 anti-phosphotyrosine antibody (lower panel). PY20 anti-phosphotyrosine antibody was used to confirm dephosphorylation of sperm protein as control. Note that MN9 antigenicity remained after CIAP treatment (upper panel). The fact that immunostaining of MN9 antibody remained after CIAP treatment, while that of PY20 antibody decreased (FIG. 4A), suggests that the epitope of the MN9 antibody was not phosphorylated.

Evaluation of Equatorin Glycosylation by Mobility Shift Assays

Since equatorin was detected by Pro-Q Emerald glycoprotein staining, cauda sperm extracts were treated with PNGase F and neuraminidase to determine whether equatorin was glycosylated and whether N-glycosylation or the sialic acid moiety was involved in the epitope region of the MN9 antibody. The enzymatically treated samples were subjected to Western blot analysis with the MN9 antibody (FIG. 4B). In lanes 1-4, equatorin in the cauda sperm extract analyzed by Western blot (15% gel) with MN9 antibody. The same amounts of PNGase F and neuraminidase treated samples were loaded in each lane: lane 1—without glycosidase treatment; lane 2—treatment with PNGase F only; lane 3—treatment with neuraminidase only; lane 4—treatment with PNGase F and neuraminidase. Mobility shifts were observed by both PNGase and neuraminidase treatment, but the MN9 antigenicity remained. PNGase F treatment reduced the molecular size of the two major bands of equatorin by approximately 2 kDa: the upper band went from 50 kDa to 48 kDa, and the lower band went from 40 kDa to 38 kDa (FIG. 4B, lanes 1 and 2). In addition, the MN9 antibody recognized only a single 27 kDa band after neuraminidase treatment (FIG. 4B, lanes 3 and 4). It is currently unclear whether this band is the long or short form. Thus, equatorin has an N-glycan with a sialylated O-glycan; i.e., it is a 40-50 kDa N,O-sialoglycoprotein. Interestingly, MN9 antigenicity was not eliminated by treatment with PNGase F and neuraminidase, suggesting that the MN9 epitope contains neither an N-linked carbohydrate nor a sialic acid moiety in the epitope region. In order to assess the involvement of O-glycosylation in MN9 antigenicity, recombinant equatorin was expressed in HEK293T cells in the presence of the O-glycosylation inhibitor Benzyl-α-GalNAc. Same amounts of the cultured cell extracts were loaded in each lane and separated in 12.5% gel. The blots were immunostained with MN9 antibody (FIG. 4C top panel) and $EQ_{70-83}$ antibody (FIG. 4C middle panel). The immunostained bands were analyzed with densitometry (see Materials and Methods) and shown in bar graph (FIG. 4C bottom panel). Numbers on the lanes indicate the concentration of Benzyl-α-GalNAc. Error bars indicate ±SD of three independent experiments. Relative MN9 antigenicity (MN9/$EQ_{70-83}$) decreased as Benzyl-α-GalNAc concentration increased.

The relative ratio of MN9/$EQ_{70-83}$ decreased in a dose-dependent manner with increasing concentrations of the Benzyl-α-GalNAc inhibitor as shown in the bar graph (FIG. 4C), suggesting the involvement of O-glycosylation in the MN9 epitope.

Determination of the Orientation of the Equatorin Epitope Region

C-terminally EGFP-tagged equatorin was transfected into HEK293T cells, and the transfected cells were examined by IIF under antibody-non-permeabilized or antibody-permeabilized conditions. Images a-f of FIG. 5A depict results of monitoring by IIF microscopy of EGFP-tagged equatorin. Images c-f of FIG. 5A depict results of 4% PFA fixation under non-permeabilized condition. Images g and h of FIG. 5A depict results of 4% PFA fixation under permeabilized condition. Hoechest 33258 counterstaining was used for the nucleus, and appear as ball-shaped figures in the images (represented in blue when the images are shown in color). Anti-$EQ_{70-83}$ antibody is shown in lighter shading dispersed around and partially within the ball-shaped figures in image a (represented in red when the figures are shown in color), MN9 antibody is shown in lighter shading dispersed around and partially within two of the ball-shaped figures in image c (represented in red when the figures are shown in color), and anti-GFP antibody is shown in lighter shading dispersed around and at the outer periphery of one of the ball-shaped figures in images e and g (represented in red when the figures are shown in color). C-terminally EGFP-tagged equatorin in transfected cells is shown in lighter shading dispersed around and partially within the ball shaped figures in images b, d, f, and h (shown in green when the figures are shown in color). Bar=10 μm. Ab; antibody. Under non-permeabilized conditions, both the $EQ_{70-83}$ antibody and MN9 antibody detected EGFP-tagged equatorin (FIG. 5A, a-d), while the anti-GFP antibody could not recognize EGFP-tagged equatorin (FIGS. 5A, e and f). Under permeabilized conditions, the anti-GFP antibody detected EGFP-tagged equatorin (FIGS. 5A, g and h).

Determination of the Amino Acid Residue Bearing the Post-translational Modification Essential for the MN9 Epitope The results in FIG. 5A suggest that equatorin is a type 1 transmembrane protein, with the MN9 epitope localized on the N-terminal side facing the external surface (FIG. 5A). Therefore, to identify the exact amino acid position at which the post-translational modification essential for MN9 epitope occurs, a partial amino acid sequence (indicated by Δ) of equatorin was first deleted, the construct was transfected into HEK293T cells, and the immunostaining loss was evaluated using Western blot analysis (FIG. 5B). The MN9 antibody detected EQT(L)Δ21-50-EGFP and EQT(L)Δ31-100-EGFP but could not detect EQT(L)Δ31-146-EGFP (FIG. 5B, upper panel). The positive control anti-GFP antibody detected all samples (FIG. 5B, lower panel). The GFP bands that ran lower than the MN9 band were degradation products (FIG. 5B); since GFP is highly resistant to proteases [39], the GFP itself maintained its antigenicity, while the equatorin portion of the EGFP-tagged equatorin protein was degraded, eliminating the MN9 antigenicity.

Figure 4:
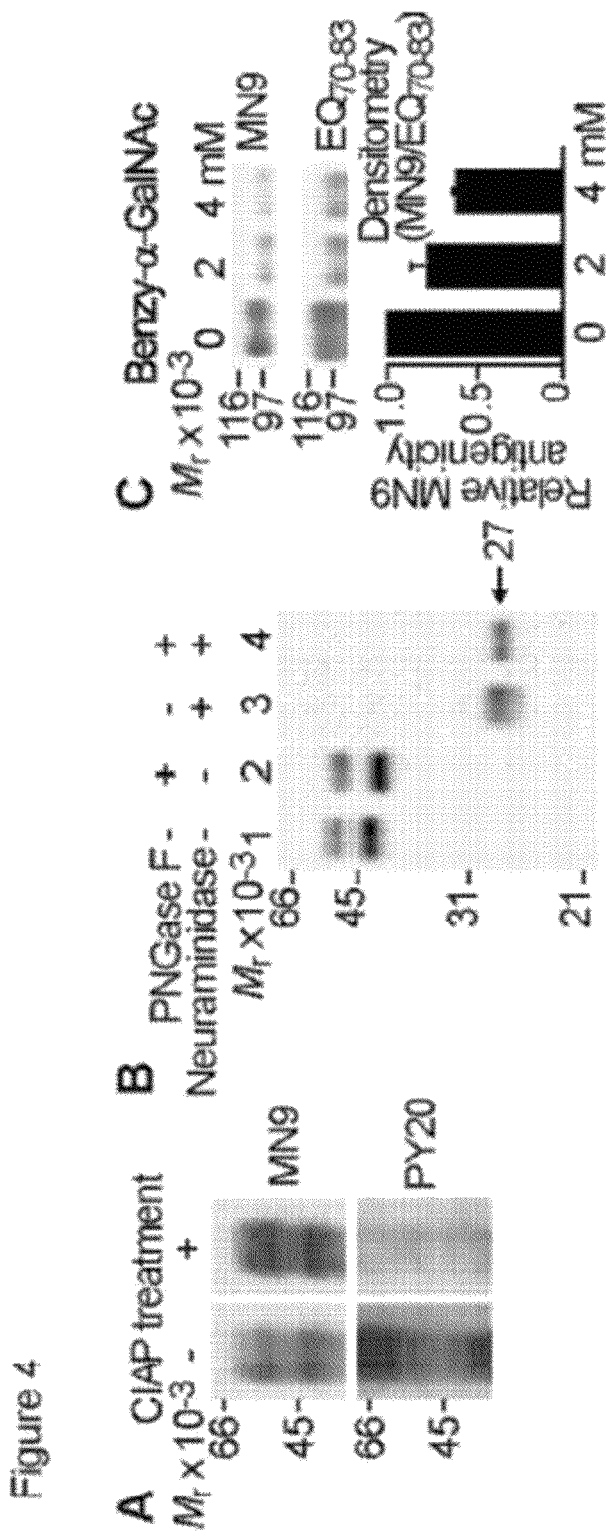
FIG. 4A. Immunostaining of MN9 antibody-analyses of phosphorylation and glycosylation status of equatorin FIG. 4B. Western blot analysis of glycosylation status by mobility shift assay using glycosidase treatment.
FIG. 4C. Western blot analysis of glycosylation status by the effect of O-glycosylation inhibitor Benzyl-α-GalNAc on MN9 epitope using EQT(L)-EGFP expressed in HEK293T cells; immunostaining with MN9 antibody (top panel); $EQ_{70-83}$ antibody (middle panel); immunostained bands were analyzed with densitometry and shown in bar graph (bottom panel).

Based on the results in FIGS. 4 and 5B, it was hypothesized that O-glycosylation at amino acid residues from 101 to 146 was involved in the MN9 epitope. Since there were two serine and three threonine residues that were not detected by LC-MS/MS analysis in this region (FIG. 2), we analyzed serine and threonine single amino acid substitution mutant proteins by Western blot (FIG. 5C). The equatorins were intentionally overloaded to avoid the false negative signals due to the low concentration, but this concomitantly caused protein degradation, showing smeared bands. Same amounts of the cultured cell extracts were loaded in each lane in each experiment, for FIG. 5B and FIG. 5C. The MN9 antibody detected all mutant proteins except the T138A mutant. This suggested that post-translational modification occurs on the threonine 138 and that this modification is involved in the MN9 epitope region.

Immunogold Electron Microscopy

Finally, the localization of equatorin was identified by immunogold electron microscopy using the MN9 antibody (FIG. 6A and FIG. 6B), preembedding method after freeze-thawing. FIG. 6A depicts an image of the anterior acrosome region. The immunogold particles (5 nm gold arrowheads) are rich on the inner acrosomal membrane (IAM), facing the acorosome lumen (acrosomal lumen indicated by asterisks), but poor (no gold particles in this photograph) on the outer acrosomal membrane (OAM). The OAM is partially broken (double arrowheads) due to the freeze-thawing treatment in this photograph, which allowed penetration of immunogold particles to the acrosome membrane. The immunogold particles are never present on the plasma membrane (PM). FIG. 6B depicts an image of the posterior acrosome region (equatorial segment). The immunogold particles (10 nm gold) are present on both the IAM (arrowheads) and OAM (double arrowheads), where the particles appear to associate with electron-dense substances facing the narrowed internal lumen. Electron-dense perinuclear substances are found between the IAM and nucleus (N). Equatorin was found to be enriched on the inner acrosomal membrane but minimal on the outer acrosomal membrane; this was typically seen in the anterior acrosome region (FIG. 6A). In contrast, equatorin was enriched on both the inner and outer acrosomal membranes in the posterior acrosome region (equatorial segment) (FIG. 6B). Immunogold particles were never observed on the plasma membrane in intact sperm (FIG. 6A).

FIG. 7 shows a schematic drawing of sperm head to show the localization of equatorin in acrosome. The MN9 epitope is present on both the outer acrosomal membrane (OAM) and the inner acrosomal membrane (IAM). The boxed area of the equatorial segment (ES) is enlarged at the right side; the N-terminus of equatorin faces the acrosomal lumen before acrosome reaction (FIG. 6). AA, anterior acrosome; PM, plasma membrane.

FIG. 8A shows western blot analysis (10% gel) with MN9 antibody. Equatorin from cauda epididymal sperm had broad apparent molecular weight of 40-50 kDa (lane 1). Equatorin migrated to 40 kDa band after 0.1% Triton X-100 treatment (lane 2), although equatorin was not solubilized in 0.1% Triton X-100 (lane 3). After 0.1% Triton X-100 treatment, 40 kDa equatorin solubilized in SDS-EDTA buffer (lane 4). FIG. 8B shows a sample preparation diagram. Lane 1; whole sperm without treatment were directly solubilized in SDS sample buffer. Lane 2; whole sperm suspended in 0.1% Triton X-100 were solubilized in SDS sample buffer. Lane 3; supernatant after centrifugation of sperm suspension in 0.1% Triton X-100. Lane 4; supernatant after centrifugation of precipitate (lane 3 sample preparation) solubilized in SDS lysis solution. Triton X-100 treatment enabled 40-50 kDa equatorin to be focused as 40 kDa single band. This focusing facilitated the efficient purification of equatorin by immunoprecipitation.

To determine specificity of $EQ_{70-83}$ antibody, Western blot analysis (12.5% gel) was conducted $EQ_{70-83}$ antibody (FIG. 9A). $EQ_{70-83}$ antibody recognized the same bands that the MN9 antibody recognized (FIG. 1A). FIG. 9B shows IIF microscopy of cauda epididymal sperm with $EQ_{70-83}$ and MN9 antibodies. Acrosome intact sperm are shown in images a, d and g. Acrosome reacted sperm are shown in images b, e and h. Triton X-100 permeabilized sperm are shown in c, f and i. $EQ_{70-83}$ antibody is shown as the leaf-shaped figure in images b-c (represented in red when the figures are shown in color). MN9 antibody is shown as the leaf-shaped figure in images e-f (represented in green when the figures are shown in color). Merged images of $EQ_{70-83}$ antibody, MN9 antibody and differential interference contrast images are shown in images g-i. Both $EQ_{70-83}$ and MN9 antibodies recognized the equatorial segment of acrosome-reacted sperm and acrosomal membrane-permeabilized sperm, but did not recognize acrosomal membrane-intact sperm. Bar=1 μm.

Figure 10:
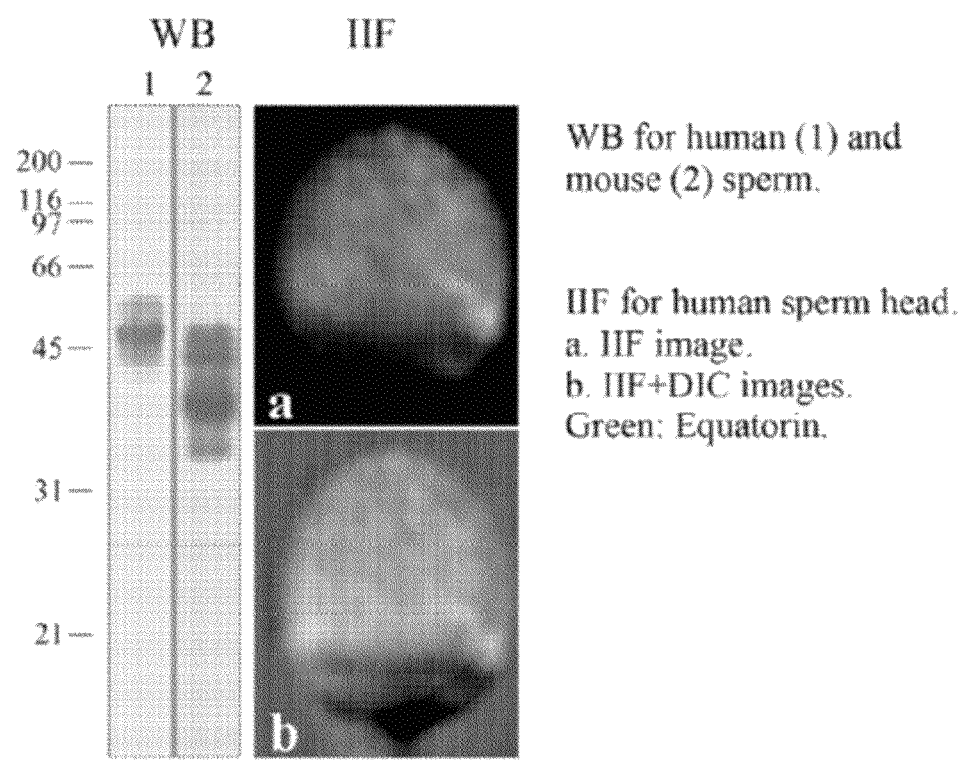
FIG. 10. Western blot analysis for mouse and human sperm and IIF microscopy for human sperm head.

FIG. 10 shows western blot analysis for mouse and human sperm and images a and b show IIF microscopy images for human sperm head without DIC (image a) and with DIC (image b).

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A method of identifying a fertilization inhibitor, comprising selecting a test compound that binds to a region of mouse equatorin that contains an O-glycosylated threonine residue located at position 138 of the amino acid sequence of SEQ ID NO: 2 or SEQ ID NO: 3, or a region of human equatorin that contains an O-glycosylated threonine residue located at position 136 of the amino acid sequence of SEQ ID NO: 5, as a candidate fertilization inhibitor.

2. The method according to claim 1, wherein said region of mouse equatorin is a region comprising the amino acid sequence from position 101 to position 146 in the amino acid sequence of SEQ ID NO: 2 or SEQ ID NO: 3 of mouse equatorin, and said region of human equatorin is a region comprising the amino acid sequence from position 92 to position 144 in the amino acid sequence of SEQ ID NO: 5 of human equatorin.

3. The method according to claim 1, wherein the method further comprises the following steps:
   (1) contacting mouse equatorin or human equatorin with the test compound, and
   (2) assaying for binding of an antibody that recognizes said region to the mouse equatorin or the human equatorin, wherein the selecting comprises selecting the test compound that reduces the binding compared to binding of the antibody to mouse equatorin or human equatorin without contacting with the test compound.

4. The method according to claim 3, wherein said antibody has an effect of inhibiting fertilization.

5. The method according to claim 3, wherein said antibody is an antibody that recognizes said region of mouse equatorin.

6. The method according to claim 3, wherein the mouse equatorin or the human equatorin is expressed in cultured cells.

7. The method according to claim 3, wherein the mouse equatorin is a partial peptide of mouse equatorin that comprises sequential amino acid residues from position 101 to position 146 of the amino acid sequence of SEQ ID NO: 2 or SEQ ID NO: 3 and contains an O-glycosylated threonine residue located at position 138 of the amino acid sequence of SEQ ID NO: 2 or SEQ ID NO: 3.

8. The method according to claim 3, wherein the human equatorin is a partial peptide of human equatorin that comprises sequential amino acid residues from position 92 to position 144 of the amino acid sequence of SEQ ID NO: 5 and contains an O-glycosylated threonine residue located at position 136 of the amino acid sequence of SEQ ID NO: 5.

9. The method according to claim 3, wherein the method further comprises steps of contacting the candidate fertilization inhibitor with male germ cells and female germ cells, assaying for fertilization between the male germ cells and female germ cells, and identifying the candidate fertilization inhibitor that inhibits the fertilization as a fertilization inhibitor.

* * * * *

SEQUENCE LISTING

```
<160> NUMBER OF SEQ ID NOS: 32

<210> SEQ ID NO 1
<211> LENGTH: 1014
<212> TYPE: DNA
<213> ORGANISM: mus musculus
<220> FEATURE:
<221> NAME/KEY: misc_feature
<223> OTHER INFORMATION: mouse equatorin gene

<400> SEQUENCE: 1
atggatttta tactgttgat cattttatct ggggttttcc tcccagacat tatcagtcta      60
cagcccattg tgggacagga gcctggtgtg acactttcag atgaagaaca gtattatgca     120
gatgaagaaa ataatacaga tgggaattct gttgcttac ataaattgga agagaatgaa     180
atggacactc ctgccaatga gaaaactggc aattattata aagacataaa acaatatgtg     240
ttcaccacac caaacataaa aggttctgaa gtatctgtga ctgccacaac taacctggaa     300
tttgctgtga agaagaacta taaagccagc aaaccaactg ccagtggaga agaagaaaaa     360
cctagtgaat cctctcgtaa aacctcaacc cccaatatac ctgcattttg gacaatatta     420
tctaaagctg taaatgaaac agcagtgagc atggatgata aagatcaatt tttttcaacca    480 attccagcct cagatttgaa tgctaccaat gaagacaaac tgtcagagct cgaggaaatc     540
aagctgaagt taatgctggg gatctcgctg atgacactgg ttctgctaat cccctcttg     600 atattctgct ttgccacact gtacaaactg agacacctac gtgacaaaag ttatgagagt     660
caatactccg tcaacccaga gctggcaact ctatcttact tccatccaac agaaggtgtg     720
tcagatacat cttttttcgaa aagtgcagac agcaactctt attgggtcca caattcttca    780
gagatgaggc gatcaaggac aagaaggtca aaatctaaac ctatggattt ttctgcaggc     840
tccaatcaaa cagtcttaac cgacgagtca agcttcctcc ctcctgagga gacaagattc     900
ctccttcctg aggagccggg taaggagctc atcgttgaga gaggccctat gcaggcaatg     960
aatgagattg atgcccagct gttgttgaac aaggaaggat caccgagtaa ttaa           1014

<210> SEQ ID NO 2
<211> LENGTH: 296
<212> TYPE: PRT
<213> ORGANISM: mus musculus
<220> FEATURE:
<221> NAME/KEY: misc_feature
<223> OTHER INFORMATION: mouse equatorin short form

<400> SEQUENCE: 2

Met Asp Phe Ile Leu Leu Ile Ile Leu Ser Gly Val Phe Leu Pro Asp
 1               5                  10                  15

Ile Ile Ser Leu Gln Pro Ile Val Gly Gln Glu Pro Gly Val Thr Leu
            20                  25                  30

Ser Asp Glu Glu Gln Tyr Tyr Ala Asp Glu Glu Asn Asn Thr Asp Gly
        35                  40                  45

Asn Ser Val Ala Leu His Lys Leu Glu Glu Asn Glu Met Asp Thr Pro
    50                  55                  60

Ala Asn Glu Lys Thr Gly Asn Tyr Tyr Lys Asp Ile Lys Gln Tyr Val
```

```
                 65                  70                  75                  80
Phe Thr Thr Pro Asn Ile Lys Gly Ser Glu Val Ser Val Thr Ala Thr
                     85                  90                  95

Thr Asn Leu Glu Phe Ala Val Lys Lys Asn Tyr Lys Ala Ser Lys Pro
                100                 105                 110

Thr Ala Ser Gly Glu Glu Glu Lys Pro Ser Glu Ser Ser Arg Lys Thr
                115                 120                 125

Ser Thr Pro Asn Ile Pro Ala Phe Trp Thr Ile Leu Ser Lys Ala Val
            130                 135                 140

Asn Glu Thr Ala Val Ser Met Asp Asp Lys Asp Gln Phe Phe Gln Pro
145                 150                 155                 160

Ile Pro Ala Ser Asp Leu Asn Ala Thr Asn Glu Asp Lys Leu Ser Glu
                165                 170                 175

Leu Glu Glu Ile Lys Leu Lys Leu Met Leu Gly Ile Ser Leu Met Thr
                180                 185                 190

Leu Val Leu Leu Ile Pro Leu Leu Ile Phe Cys Phe Ala Thr Leu Tyr
                195                 200                 205

Lys Leu Arg His Leu Arg Asp Lys Ser Tyr Glu Ser Gln Tyr Ser Val
                210                 215                 220

Asn Pro Glu Leu Ala Thr Leu Ser Tyr Phe His Pro Thr Glu Gly Ser
225                 230                 235                 240

Asn Gln Thr Val Leu Thr Asp Glu Ser Ser Phe Leu Pro Pro Glu Glu
                245                 250                 255

Thr Arg Phe Leu Leu Pro Glu Glu Pro Gly Lys Glu Leu Ile Val Glu
                260                 265                 270

Arg Gly Pro Met Gln Ala Met Asn Glu Ile Asp Ala Gln Leu Leu Leu
                275                 280                 285

Asn Lys Glu Gly Ser Pro Ser Asn
                290                 295

<210> SEQ ID NO 3
<211> LENGTH: 337
<212> TYPE: PRT
<213> ORGANISM: mus musculus
<220> FEATURE:
<221> NAME/KEY: misc_feature
<223> OTHER INFORMATION: mouse equatorin long form

<400> SEQUENCE: 3

Met Asp Phe Ile Leu Leu Ile Ile Leu Ser Gly Val Phe Leu Pro Asp
1               5                   10                  15

Ile Ile Ser Leu Gln Pro Ile Val Gly Gln Glu Pro Gly Val Thr Leu
                20                  25                  30

Ser Asp Glu Glu Gln Tyr Tyr Ala Asp Glu Glu Asn Asn Thr Asp Gly
            35                  40                  45

Asn Ser Val Ala Leu His Lys Leu Glu Glu Asn Glu Met Asp Thr Pro
50                  55                  60

Ala Asn Glu Lys Thr Gly Asn Tyr Tyr Lys Asp Ile Lys Gln Tyr Val
65                  70                  75                  80

Phe Thr Thr Pro Asn Ile Lys Gly Ser Glu Val Ser Val Thr Ala Thr
                85                  90                  95

Thr Asn Leu Glu Phe Ala Val Lys Lys Asn Tyr Lys Ala Ser Lys Pro
                100                 105                 110

Thr Ala Ser Gly Glu Glu Glu Lys Pro Ser Glu Ser Ser Arg Lys Thr
                115                 120                 125

Ser Thr Pro Asn Ile Pro Ala Phe Trp Thr Ile Leu Ser Lys Ala Val
```

```
              130                 135                 140
Asn Glu Thr Ala Val Ser Met Asp Asp Lys Asp Gln Phe Phe Gln Pro
145                 150                 155                 160

Ile Pro Ala Ser Asp Leu Asn Ala Thr Asn Glu Asp Lys Leu Ser Glu
                165                 170                 175

Leu Glu Glu Ile Lys Leu Lys Leu Met Leu Gly Ile Ser Leu Met Thr
                    180                 185                 190

Leu Val Leu Leu Ile Pro Leu Leu Ile Phe Cys Phe Ala Thr Leu Tyr
                195                 200                 205

Lys Leu Arg His Leu Arg Asp Lys Ser Tyr Glu Ser Gln Tyr Ser Val
                210                 215                 220

Asn Pro Glu Leu Ala Thr Leu Ser Tyr Phe His Pro Thr Glu Gly Val
225                 230                 235                 240

Ser Asp Thr Ser Phe Ser Lys Ser Ala Asp Ser Asn Ser Tyr Trp Val
                    245                 250                 255

His Asn Ser Ser Glu Met Arg Arg Ser Arg Thr Arg Arg Ser Lys Ser
                260                 265                 270

Lys Pro Met Asp Phe Ser Ala Gly Ser Asn Gln Thr Val Leu Thr Asp
                    275                 280                 285

Glu Ser Ser Phe Leu Pro Pro Glu Thr Arg Phe Leu Pro Glu
290                 295                 300

Glu Pro Gly Lys Glu Leu Ile Val Glu Arg Gly Pro Met Gln Ala Met
305                 310                 315                 320

Asn Glu Ile Asp Ala Gln Leu Leu Leu Asn Lys Glu Gly Ser Pro Ser
                    325                 330                 335

Asn

<210> SEQ ID NO 4
<211> LENGTH: 885
<212> TYPE: DNA
<213> ORGANISM: homosapiens
<220> FEATURE:
<221> NAME/KEY: misc_feature
<223> OTHER INFORMATION: human equatorin gene

<400> SEQUENCE: 4
atgaatttta tattgtttat ttttatacct ggagtttttt ccttaaaaag tagcactttg      60
aagcctacta ttgaagcatt gcctaatgtg ctacctttaa atgaagatgt taataagcag     120
gaagaaaaga atgaagatca tactcccaat tatgctcctg ctaatgagaa aaatggcaat     180
tattataaag atataaaaca atatgtgttc acaacacaaa atccaaatgg cactgagtct     240
gaaatatctg tgagagccac aactgacctg aatttttgctc taaaaaacga taaaactgtc     300
aatgcaacta catatgaaaa atccaccatt gaagaagaaa caactactag cgaaccctct     360
cataaaaata ttcaaagatc aaccccaaac gtgcctgcat tttggacaat gttagctaaa     420
gctataaatg aacagcagt ggtcatggat gataaagatc aattatttca cccaattcca     480
gagtctgatg tgaatgctac acagggagaa atcagccag atctagagga tctgaagatc     540
aaaataatgc tgggaatctc gttgatgacc ctcctcctct tgtggtcct cttggcattc     600 tgtagtgcta cactgtacaa actgaggcat ctgagttata aagttgtga gagtcagtac     660 tctgtcaacc cagagctggc cacgatgtct tactttcatc catcagaagg tgtttcagat     720
acatcctttt ccaagagtgc agagagcagc acatttttgg gtaccacttc ttcagatatg     780
agaagatcag gcacaagaac atcagaatct aagataatga cggatatcat ttccataggc     840
tcaaataatg agatgcatga aaacgatgag tcggttaccc ggtga                    885
```

<210> SEQ ID NO 5
<211> LENGTH: 294
<212> TYPE: PRT
<213> ORGANISM: homosapiens
<220> FEATURE:
<221> NAME/KEY: misc_feature
<223> OTHER INFORMATION: human equatorin

<400> SEQUENCE: 5

Met Asn Phe Ile Leu Phe Ile Phe Ile Pro Gly Val Phe Ser Leu Lys
1               5                   10                  15

Ser Ser Thr Leu Lys Pro Thr Ile Glu Ala Leu Pro Asn Val Leu Pro
            20                  25                  30

Leu Asn Glu Asp Val Asn Lys Gln Glu Glu Lys Asn Glu Asp His Thr
        35                  40                  45

Pro Asn Tyr Ala Pro Ala Asn Glu Lys Asn Gly Asn Tyr Tyr Lys Asp
    50                  55                  60

Ile Lys Gln Tyr Val Phe Thr Thr Gln Asn Pro Asn Gly Thr Glu Ser
65                  70                  75                  80

Glu Ile Ser Val Arg Ala Thr Thr Asp Leu Asn Phe Ala Leu Lys Asn
                85                  90                  95

Asp Lys Thr Val Asn Ala Thr Thr Tyr Glu Lys Ser Thr Ile Glu Glu
            100                 105                 110

Glu Thr Thr Thr Ser Glu Pro Ser His Lys Asn Ile Gln Arg Ser Thr
        115                 120                 125

Pro Asn Val Pro Ala Phe Trp Thr Met Leu Ala Lys Ala Ile Asn Gly
    130                 135                 140

Thr Ala Val Val Met Asp Asp Lys Asp Gln Leu Phe His Pro Ile Pro
145                 150                 155                 160

Glu Ser Asp Val Asn Ala Thr Gln Gly Glu Asn Gln Pro Asp Leu Glu
                165                 170                 175

Asp Leu Lys Ile Lys Ile Met Leu Gly Ile Ser Leu Met Thr Leu Leu
            180                 185                 190

Leu Phe Val Val Leu Leu Ala Phe Cys Ser Ala Thr Leu Tyr Lys Leu
        195                 200                 205

Arg His Leu Ser Tyr Lys Ser Cys Glu Ser Gln Tyr Ser Val Asn Pro
    210                 215                 220

Glu Leu Ala Thr Met Ser Tyr Phe His Pro Ser Glu Gly Val Ser Asp
225                 230                 235                 240

Thr Ser Phe Ser Lys Ser Ala Glu Ser Ser Thr Phe Leu Gly Thr Thr
                245                 250                 255

Ser Ser Asp Met Arg Arg Ser Gly Thr Arg Thr Ser Glu Ser Lys Ile
            260                 265                 270

Met Thr Asp Ile Ile Ser Ile Gly Ser Asn Asn Glu Met His Glu Asn
        275                 280                 285

Asp Glu Ser Val Thr Arg
    290

<210> SEQ ID NO 6
<211> LENGTH: 14
<212> TYPE: PRT
<213> ORGANISM: artificial
<220> FEATURE:
<223> OTHER INFORMATION: a synthetic peptide consisting of 14-residue
      partial sequence of equatorin

<400> SEQUENCE: 6

-continued

```
Gly Asn Tyr Tyr Lys Asp Ile Lys Gln Tyr Val Phe Thr Thr
1               5                   10
```

```
<210> SEQ ID NO 7
<211> LENGTH: 22
<212> TYPE: DNA
<213> ORGANISM: artificial
<220> FEATURE:
<223> OTHER INFORMATION: designed oligonucleotide for use as a primer

<400> SEQUENCE: 7
aatgctgggg atctcgctga tg                                              22

<210> SEQ ID NO 8
<211> LENGTH: 25
<212> TYPE: DNA
<213> ORGANISM: artificial
<220> FEATURE:
<223> OTHER INFORMATION: designed oligonucleotide for use as a primer

<400> SEQUENCE: 8
attactcggt gatccttcct tgttc                                           25

<210> SEQ ID NO 9
<211> LENGTH: 20
<212> TYPE: DNA
<213> ORGANISM: artificial
<220> FEATURE:
<223> OTHER INFORMATION: designed oligonucleotide for use as a primer

<400> SEQUENCE: 9
accacagtcc atgccatcac                                                 20

<210> SEQ ID NO 10
<211> LENGTH: 20
<212> TYPE: DNA
<213> ORGANISM: artificial
<220> FEATURE:
<223> OTHER INFORMATION: designed oligonucleotide for use as a primer

<400> SEQUENCE: 10
tccaccaccc tgttgctgta                                                 20

<210> SEQ ID NO 11
<211> LENGTH: 30
<212> TYPE: DNA
<213> ORGANISM: artificial
<220> FEATURE:
<223> OTHER INFORMATION: designed oligonucleotide for use as a primer

<400> SEQUENCE: 11
ccccgcgtcg acgtaattac tcggtgatcc                                      30

<210> SEQ ID NO 12
<211> LENGTH: 30
<212> TYPE: DNA
<213> ORGANISM: artificial
<220> FEATURE:
<223> OTHER INFORMATION: designed oligonucleotide for use as a primer

<400> SEQUENCE: 12
cgcggatcca tggattttat actgttgatc                                      30

<210> SEQ ID NO 13
<211> LENGTH: 23
<212> TYPE: DNA
<213> ORGANISM: artificial
```

```
<220> FEATURE:
<223> OTHER INFORMATION: designed oligonucleotide for use as a primer

<400> SEQUENCE: 13
tgagatccgg ctgctaacaa agc                                              23

<210> SEQ ID NO 14
<211> LENGTH: 28
<212> TYPE: DNA
<213> ORGANISM: artificial
<220> FEATURE:
<223> OTHER INFORMATION: designed oligonucleotide for use as a primer

<400> SEQUENCE: 14
attactcggt gatccttcct tgttcaac                                         28

<210> SEQ ID NO 15
<211> LENGTH: 24
<212> TYPE: DNA
<213> ORGANISM: artificial
<220> FEATURE:
<223> OTHER INFORMATION: designed oligonucleotide for use as a primer

<400> SEQUENCE: 15
gctccaatca aacagtctta accg                                             24

<210> SEQ ID NO 16
<211> LENGTH: 25
<212> TYPE: DNA
<213> ORGANISM: artificial
<220> FEATURE:
<223> OTHER INFORMATION: designed oligonucleotide for use as a primer

<400> SEQUENCE: 16
cttctgttgg atggaagtaa gatag                                            25

<210> SEQ ID NO 17
<211> LENGTH: 24
<212> TYPE: DNA
<213> ORGANISM: artificial
<220> FEATURE:
<223> OTHER INFORMATION: designed oligonucleotide for use as a primer

<400> SEQUENCE: 17
gttgctttac ataaattgga agag                                             24

<210> SEQ ID NO 18
<211> LENGTH: 29
<212> TYPE: DNA
<213> ORGANISM: artificial
<220> FEATURE:
<223> OTHER INFORMATION: designed oligonucleotide for use as a primer

<400> SEQUENCE: 18
tagactgata atgtctggga ggaaaaccc                                        29

<210> SEQ ID NO 19
<211> LENGTH: 27
<212> TYPE: DNA
<213> ORGANISM: artificial
<220> FEATURE:
<223> OTHER INFORMATION: designed oligonucleotide for use as a primer

<400> SEQUENCE: 19
tttgctgtga agaagaacta taaagcc                                          27
```

```
<210> SEQ ID NO 20
<211> LENGTH: 25
<212> TYPE: DNA
<213> ORGANISM: artificial
<220> FEATURE:
<223> OTHER INFORMATION: designed oligonucleotide for use as a primer

<400> SEQUENCE: 20
cacaccagcc tcctgtccca caatg                                        25

<210> SEQ ID NO 21
<211> LENGTH: 27
<212> TYPE: DNA
<213> ORGANISM: artificial
<220> FEATURE:
<223> OTHER INFORMATION: designed oligonucleotide for use as a primer

<400> SEQUENCE: 21
acagcagtga gcatggatga taaagat                                      27

<210> SEQ ID NO 22
<211> LENGTH: 25
<212> TYPE: DNA
<213> ORGANISM: artificial
<220> FEATURE:
<223> OTHER INFORMATION: designed oligonucleotide for use as a primer

<400> SEQUENCE: 22
cacaccagcc tcctgtccca caatg                                        25

<210> SEQ ID NO 23
<211> LENGTH: 30
<212> TYPE: DNA
<213> ORGANISM: artificial
<220> FEATURE:
<223> OTHER INFORMATION: designed oligonucleotide for use as a primer

<400> SEQUENCE: 23
ctctcgtaaa gcctcaaccc ccaatatacc                                   30

<210> SEQ ID NO 24
<211> LENGTH: 30
<212> TYPE: DNA
<213> ORGANISM: artificial
<220> FEATURE:
<223> OTHER INFORMATION: designed oligonucleotide for use as a primer

<400> SEQUENCE: 24
ggtatattgg gggttgaggc tttacgagag                                   30

<210> SEQ ID NO 25
<211> LENGTH: 30
<212> TYPE: DNA
<213> ORGANISM: artificial
<220> FEATURE:
<223> OTHER INFORMATION: designed oligonucleotide for use as a primer

<400> SEQUENCE: 25
ctctcgtaaa accgcaaccc ccaatatacc                                   30

<210> SEQ ID NO 26
<211> LENGTH: 30
<212> TYPE: DNA
<213> ORGANISM: artificial
<220> FEATURE:
<223> OTHER INFORMATION: designed oligonucleotide for use as a primer

<400> SEQUENCE: 26
```

```
ggtatattgg gggttgcggt tttacgagag                                    30

<210> SEQ ID NO 27
<211> LENGTH: 30
<212> TYPE: DNA
<213> ORGANISM: artificial
<220> FEATURE:
<223> OTHER INFORMATION: designed oligonucleotide for use as a primer

<400> SEQUENCE: 27
ctctcgtaaa acctcagccc ccaatatacc                                    30

<210> SEQ ID NO 28
<211> LENGTH: 30
<212> TYPE: DNA
<213> ORGANISM: artificial
<220> FEATURE:
<223> OTHER INFORMATION: designed oligonucleotide for use as a primer

<400> SEQUENCE: 28
ggtatattgg gggctgaggt tttacgagag                                    30

<210> SEQ ID NO 29
<211> LENGTH: 29
<212> TYPE: DNA
<213> ORGANISM: artificial
<220> FEATURE:
<223> OTHER INFORMATION: designed oligonucleotide for use as a primer

<400> SEQUENCE: 29
cctgcatttt gggcaatatt atctaaagc                                     29

<210> SEQ ID NO 30
<211> LENGTH: 29
<212> TYPE: DNA
<213> ORGANISM: artificial
<220> FEATURE:
<223> OTHER INFORMATION: designed oligonucleotide for use as a primer

<400> SEQUENCE: 30
gctttagata atattgccca aaatgcagg                                     29

<210> SEQ ID NO 31
<211> LENGTH: 28
<212> TYPE: DNA
<213> ORGANISM: artificial
<220> FEATURE:
<223> OTHER INFORMATION: designed oligonucleotide for use as a primer

<400> SEQUENCE: 31
gcattttgga caatattagc taaagctg                                      28

<210> SEQ ID NO 32
<211> LENGTH: 28
<212> TYPE: DNA
<213> ORGANISM: artificial
<220> FEATURE:
<223> OTHER INFORMATION: designed oligonucleotide for use as a primer

<400> SEQUENCE: 32
cagctttagc taatattgtc caaaatgc                                      28
```